United States Patent
Shintou et al.

(10) Patent No.: US 10,278,965 B2
(45) Date of Patent: May 7, 2019

(54) METHOD OF DETECTING CANCER STEM CELL, METHOD OF SCREENING CANCER STEM CELL, AND METHOD OF INHIBITING CANCER STEM CELL

(71) Applicant: CANON KABUSHIKI KAISHA, Tokyo (JP)

(72) Inventors: Taichi Shintou, Saitama (JP); Tsuyoshi Nomoto, Tokyo (JP); Kohei Watanabe, Brookline, MA (US); Takeshi Miyazaki, Ebina (JP); Toshio Tanaka, Tsu (JP); Yasuhito Shimada, Tsu (JP); Yuhei Nishimura, Tsu (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/678,596

(22) Filed: Aug. 16, 2017

(65) Prior Publication Data
US 2017/0340622 A1 Nov. 30, 2017

Related U.S. Application Data

(62) Division of application No. 14/408,787, filed as application No. PCT/JP2013/079650 on Oct. 25, 2013.

(30) Foreign Application Priority Data

Oct. 26, 2012 (JP) ................................. 2012-236977

(51) Int. Cl.
| | |
|---|---|
| *A61K 31/4709* | (2006.01) |
| *A61K 31/403* | (2006.01) |
| *A61K 31/423* | (2006.01) |
| *A61K 31/428* | (2006.01) |
| *A61K 31/404* | (2006.01) |
| *A61K 41/00* | (2006.01) |
| *A61K 49/00* | (2006.01) |
| *C09B 23/01* | (2006.01) |
| *C09B 23/06* | (2006.01) |
| *C09B 23/08* | (2006.01) |
| *G01N 33/58* | (2006.01) |

(52) U.S. Cl.
CPC ........ *A61K 31/4709* (2013.01); *A61K 31/403* (2013.01); *A61K 31/404* (2013.01); *A61K 31/423* (2013.01); *A61K 31/428* (2013.01); *A61K 41/0038* (2013.01); *A61K 49/0032* (2013.01); *C09B 23/0008* (2013.01); *C09B 23/0016* (2013.01); *C09B 23/0025* (2013.01); *C09B 23/0033* (2013.01); *C09B 23/0066* (2013.01); *C09B 23/06* (2013.01); *C09B 23/083* (2013.01); *C09B 23/086* (2013.01); *G01N 33/582* (2013.01)

(58) Field of Classification Search
CPC .............. A61K 31/4709; A61K 31/403; A61K 31/404; A61K 31/423; A61K 31/428; A61K 41/0038; A61K 49/0032; C09B 23/0008; C09B 23/0016; C09B 23/0025; C09B 23/0033; C09B 23/0066; C09B 23/06; C09B 23/083; C09B 23/086; G01N 33/582
See application file for complete search history.

(56) References Cited

U.S. PATENT DOCUMENTS

| | | | |
|---|---|---|---|
| 4,651,739 | A | 3/1987 | Oseroff et al. |
| 5,491,151 | A | 2/1996 | Nakagawa et al. |
| 7,515,953 | B2 | 4/2009 | Madar et al. |
| 7,653,429 | B2 | 1/2010 | Madar et al. |
| 8,652,438 | B2 | 2/2014 | Nomoto et al. |
| 9,040,687 | B2 | 5/2015 | Ramaiah et al. |
| 2006/0239916 | A1 | 10/2006 | Licha et al. |
| 2009/0305410 | A1 | 12/2009 | Mao et al. |

(Continued)

FOREIGN PATENT DOCUMENTS

| | | |
|---|---|---|
| EP | 2 397 139 A1 | 12/2011 |
| JP | 54-157839 A | 12/1979 |

(Continued)

OTHER PUBLICATIONS

Crous & Abrahamse, Lung Cancer Stem Cells and Low-Intensity Laser Irradiation: A Potential Future Therapy?, 4(129) Stem Cell Research & Therapy (2013) (Year: 2013).*

(Continued)

*Primary Examiner* — Timothy R Rozof
(74) *Attorney, Agent, or Firm* — Venable LLP

(57) ABSTRACT

An object of the present invention is to provide a cancer cell inhibitory drug, particularly a cancer stem-cell inhibitory drug, or a cancer stem-cell detection probe. The present invention provides a cancer cell inhibitory drug comprising at least one compound represented by general formula (1) as an active ingredient

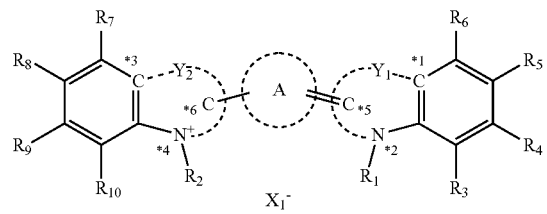

General formula (1)

12 Claims, No Drawings

(56) References Cited

U.S. PATENT DOCUMENTS

| | | |
|---|---|---|
| 2010/0166659 A1 | 7/2010 | Licha et al. |
| 2011/0189096 A1 | 8/2011 | Watanabe et al. |
| 2012/0035187 A1 | 2/2012 | Ohta et al. |
| 2012/0207683 A1 | 8/2012 | Tanaka et al. |
| 2013/0280169 A1 | 10/2013 | Watanabe et al. |
| 2014/0017722 A1 | 1/2014 | Watanabe et al. |
| 2014/0094490 A1 | 4/2014 | Ohta et al. |
| 2014/0112869 A1 | 4/2014 | Nomoto et al. |
| 2015/0274715 A1 | 10/2015 | Shintou et al. |
| 2017/0056378 A1 | 3/2017 | Shintou et al. |

FOREIGN PATENT DOCUMENTS

| | | |
|---|---|---|
| JP | 61-288872 A | 12/1986 |
| JP | 3-90025 A | 4/1991 |
| JP | 2006-512109 A | 4/2006 |
| JP | 2008-526802 A | 7/2008 |
| JP | 2010-013380 A | 1/2010 |
| JP | 2011-506673 A | 3/2011 |
| JP | 2013-518042 A | 5/2013 |
| WO | 88/03955 A1 | 6/1988 |
| WO | 2008/019139 A2 | 2/2008 |
| WO | 2009/152440 A1 | 12/2009 |
| WO | 2010/087306 A1 | 8/2010 |
| WO | 2011/089509 A1 | 7/2011 |
| WO | 2014/065440 A1 | 5/2014 |

OTHER PUBLICATIONS

Notification of Reasons for Refusal in Japanese Application No. 2013-222025 (dated Mar. 29, 2018).

Notification of Reasons for Refusal in Japanese Application No. 2013-222025 (dated Aug. 10, 2017).

E. Delaey et al., "A Comparative Study of the Photosensitizing Characteristics of Some Cyanine Dyes," 55(1) J. Photochem. Photobiol. B: Biol. 27-36 (Mar. 2000).

Sara Gosk et al., "VCAM-1 Directed Immunoliposomes Selectively Target Tumor Vasculature in Vivo," 1778(4) Biochimica et Biophysica Acta 854-863 (Jan. 2008).

Jeffrey R. Kanofsky et al., "Preferential cytotoxicity for multidrug-resistant K562 cells using the combination of a photosensitizer and a cyanine dye," 54(2-3) J. Photochem. Photobiol. B: Biol. 136-144 (Feb. 2000).

Yan Zhang et al., "Increasing Sensitivity to Arsenic Trioxide-Induced Apoptosis by Altered Telomere State," 474(2-3) Eur. J. Pharmacol. 141-147 (Jul. 2003).

Zhanxiang Wang, "Disruption of the Inhibitor of Apoptosis Protein Survivin Sensitizes Bcr-abl—Positive Cells to STI571-Induced Apoptosis," 65(18) Cancer Res. 8224-8232 (Sep. 2005).

Kawser Kassab, "Photophysical and photosensitizing properties of selected cyanines," 68(1) J. Photochem. Photobiol. B: Biol. 15-22 (Jun. 2002).

Fariba Behbod et al., "Will Cancer Stem Cells Provide New Therapeutic Targets?" 26(4) Carcinogenesis 703-711 (2004).

Michael Dean et al., "Tumour Stem Cells and Drug Resistance," 5(4) Nature Reviews Cancer 275-284 (Apr. 2005).

Xiaojun Peng et al., "Fluorescence Ratiometry and Fluorescence Lifetime Imaging: Using a Single Molecular Sensor for Dual Mode Imaging of Cellular Viscosity," 133(17) J. Am. Chem. Soc. 6626-6635 (Apr. 2011).

Cristina Encinas et al., "Synthesis and Spectroscopic Characterisation of Heptamethincyanine NIR Dyes for Their Use in Optochemical Sensors," 71(1) Dye and Pigments 28-36 (Sep. 2005).

Shuji Ikeda et al., "Hybridization-Sensitive Fluorescence Control in the Near-Infrared Wavelength Range," 9(11) Org. Biomol. Chem. 4199-4204 (Mar. 2011).

Maged Henary et al., "Near Infrared Active Heptacyanine Dyes with Unique Cancer-Imageing and Cytotoxic Properties," 22 Bioorg. Med. Chem. Lett., 1242-1246 (Nov. 2011).

Roman Mezencev et al., "Identification of Inhibitors of Ovarian Cancer Stem-Like Cells by High-Throughput Screening," 5:30 Journal of Ovarian Research 1-11 (Oct. 2012).

Ja-Young Kim et al., "Highly Selective in-vivo Imaging of Tumor as an Inflammation Site by ROS Detection Using Hydrocyanine-Cojugated, Functional Nano-Carriers," 156 J. Controlled Release 398-405 (Dec. 2011).

International Search Report in International Application No. PCT/JP2013/079650 (dated Jan. 2014).

International Preliminary Report on Patentability with Written Opinion in International Application No. PCT/JP2013/079650 (dated Apr. 2015).

Christopher Lee et al., "Photosensitization by 3,3'-Dihexyloxacarbocyanine Iodide: Specific Disruption of Microtubules and Inactivation of Organelle Motility," 55(10) Cancer Res. 2063-2069 (May 1995) (XP055190881).

Marianne Krieg et al., "Structurally Modified Trimethine Thiacarbocyanine Dyes: Effect of N-Alkyl Substituents on Antineoplastic Behavior," 51(11) Biochem. Pharmacol. 1461-1467 (Jun. 1996) (XP055081933).

Narasimhachari Narayanan et al., "A New Method for the Synthesis of Heptamethine Cyanine Dyes: Synthesis of New Near-Infrared Fluorescent Labels," 60(8) J. Org. Chem. 2391-2395 (Apr. 1995) (XP002065376).

Gerald S. Lipshutz et al., "Evaluation of Four New Carbocyanine Dyes for Photodynamic Therapy with Lasers," 104(8) Laryngoscope 996-1002 (Aug. 1994) (XP002739904).

Roxana Metzele et al., "Human Adipose Tissue-Derived Stem Cells Exhibit Proliferation Potential and Spontaneous Rhythmic Contraction After Fusion with Neonatal Rat Cardiomyocytes," 25(3) FASEB 830-839 (Nov. 2010) (XP055190866).

Extended European Search Report in European Application No. 13849936.3 (dated Jun. 8, 2015).

Communication pursuant to Article 94(3) EPC in European Application No. 13849936.3 (dated May 30, 2017).

Howard M. Shapiro, Cell Membrane Potential Analysis, Ch. 4 in Methods in Cell Biology, vol. 33: Flow Cytometry, pp. 25-37, 30 (Academic Press 1990).

Eiji Okimasu et al., "Tests of Fluorescence Changes in Tumor Cells Due to Changes in Mitochondria Energy Metabolism with Low-Toxicity NK 1507," 88 Kanko Shikiso 21-30 (1981) (CAS Abstract).

\* cited by examiner

METHOD OF DETECTING CANCER STEM CELL, METHOD OF SCREENING CANCER STEM CELL, AND METHOD OF INHIBITING CANCER STEM CELL

CROSS-REFERENCE TO RELATED APPLICATIONS

This application is a divisional application of U.S. patent application Ser. No. 14/408,787, which was the National Stage of International Application No. PCT/JP2013/079650, filed Oct. 25, 2013, which claims the benefit of Japanese Patent Application No. 2012-236977, filed Oct. 26, 2012. All of these prior applications are incorporated herein by reference in their entirety.

TECHNICAL FIELD

The present invention relates to a cancer cell inhibitory drug, particularly to a cancer stem cell inhibitory drug, and a cancer stem-cell detection probe.

BACKGROUND ART

At present, as a general cancer therapy, e.g., radiation therapy, chemotherapy, immunotherapy and surgical (excision) therapy are mentioned. The chemotherapy is a method for suppressing cancer by use of an anticancer therapeutic agent made of various types of low-molecular compounds.

The therapy using an anticancer therapeutic agent is directed to reduce the size of a solid tumor. However, the most part of a tumor is occupied by differentiated cancer cells which no longer have a function as a cancer stem cell and it is pointed out in a general anticancer agent treatment that the differentiated cancer cells are only targeted to reduce the size thereof.

Cancer has cells having nature of stem cells, called cancer stem cells.

The cancer stem cells, which were first identified in 1997 in an acute myeloid leukemia, are now increasingly found in various types of cancers including solid cancers, and recently, a new way of thinking, called "cancer stem cell hypothesis" that cancer would be developed from cancer stem cells as an origin, has been proposed (NPL 1).

According to the hypothesis, even though the most part of cancer cells are killed or excised out by applying the aforementioned therapy, if a very small number of self-reproducible cancer stem cells remain, recurrence and metastasis conceivably occur. In short, it is considered that recurrence and metastasis are caused by the remaining small amount of cancer stem cells. Accordingly, if cancer stem cells can be targeted and completely eradicated, it is expected to develop a useful therapy for preventing metastasis and recurrence of cancer.

It is pointed out that some of the cancer stem cells acquire drug resistance to an anticancer therapeutic agent (NPL 2).

At present, as a low-molecular compound for use in detection of cancer stem cells and as a therapeutic agent, a compound containing radioactive Cu-ATSM is known (PTL 1). However, the radioactive compound may affect normal cells. Therefore, when a radioactive compound is used, safety becomes a matter of concern. In addition, it is also pointed out that cancer stem cells may develop strong resistance to radiation.

In the circumstances, it has been desired to develop a drug inhibiting cancer stem cells and a compound capable of detecting cancer stem cells.

CITATION LIST

Patent Literature

PTL 1: Japanese Patent Application Laid-Open No. 2010-013380

Non Patent Literature

NPL 1: Carcinogenesis, Vol. 26, p.p. 703-711, 2005
NPL 2: Nature Review Cancer, Vol. 5, p.p. 275-284, 2005
NPL 3: Journal of the American Chemical Society, Vol. 133, p.p. 6626-6635, 2011
NPL 4: Dye and Pigments, Vol. 71, p.p. 28-36, 2005
NPL 5: Organic & Biomolecular Chemistry, Vol. 9, p.p. 4199-4204, 2011

SUMMARY OF INVENTION

Technical Problem

Cancer stem cells have high resistance to radiation therapies and chemotherapies conventionally used and are causual cells from which cancer growth, recurrence and metastasis occur. Up to present, where cancer stem cells are present cannot be clearly detected. This was a issue remaining unsolved. To completely cure cancer, it has been strongly desired to detect cancer stem cells and develop a drug inhibiting cancer cells, in particular, cancer stem cells.

Solution to Problem

The present inventors intensively made studies with a view to solving the aforementioned problem. As a result, they found that a compound represented by the following general formula (1) has an inhibitory effect on cancer cells and is selectively taken into particularly cancer stem cells among the cancer cells and inhibits them. Based on the finding, the present invention was accomplished.

Furthermore, the compound of the present invention has a luminescence property. Owing to this, the position of cancer cells can be identified (determined) by detecting luminescence of the compound selectively taken into cancer cells. Based on the finding, the present inventors arrived at the present invention. Note that, in the specification, luminescence includes fluorescence and phosphorescence. Since the compound of the present invention is taken into particularly cancer stem cells in a high ratio, cancer stem cells can be selectively detected.

More specifically, the compound of the present invention contains a compound represented by general formula (1):

General formula (1)

In general formula (1), $R_1$ and $R_2$ each independently represent an alkyl group, a carboxylalkyl group, an alkoxycarbonylalkyl group or an alkylcarbonyloxyalkyl group; $R_3$ to $R_{10}$ each independently represent a hydrogen atom, an alkyl group, an aryl group, an alkoxy group, a halogen atom, an alkoxysulfonyl group, a N-alkylsulfamoyl group, an alkyloxycarbonyl group, a carbamoyl group or a N-alkylcarbamoyl group; $R_3$ and $R_4$, $R_5$ and $R_6$, $R_7$ and $R_8$, and $R_9$ and $R_{10}$ may be each independently cyclized to form a benzene ring; $X_1^-$ represents an anionic group; $Y_1$ is a group including *1, *2 and *5 and represents any one of the followings: *1-S-*5-*2, *1-O-*5-*2, *1-C(—$R_{11}$,—$R_{12}$)-*5-*2, and *1-*5-CH=CH-*2, where $R_{11}$ and $R_{12}$ each independently represent an alkyl group, and $R_{11}$ and $R_{12}$ may bind together to form a ring; $Y_2$ is a group including *3, *4 and *6 and represents any one of the followings:
*4=*6-S-*3, *4=*6-O-*3, *4=*6-C(—$R_{51}$,—$R_{52}$)-*3, *4=*6-CH=CH-*3, and *4=CH—CH=*6-*3, where $R_{51}$ and $R_{52}$ each independently represent an alkyl group and $R_{51}$ and $R_{52}$ may bind together to form a ring; and a group including A to carbon atoms represented by *5 and *6 is represented by general formula (2) or (3).

General formula (2)

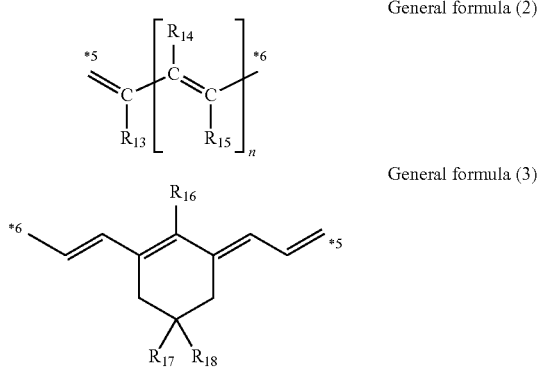

General formula (3)

(In general formula (2), $R_{13}$ to $R_{15}$ each independently represent a hydrogen atom, an alkyl group or an aryl group; and n represents an integer of 0 to 2, and in general formula (3), $R_{16}$ represents a hydrogen atom, a phenyl group, a thiol group, an alkoxy group, an aryloxy group or a halogen atom; and $R_{17}$ and $R_{18}$ each independently represent a hydrogen atom, an alkyl group or an alkyloxycarbonyl group).

Advantageous Effects of Invention

Owing to the compound provided by the present invention, growth suppression, cellular division suppression, metastasis suppression, functional inhibition and cytocidal action of cancer cells can be mediated even in sites where cancer cells are overlooked by surgical excision and hardly excised out. More specifically, the present invention provides a cancer cell inhibitory drug. Further, of the cancer cells, particularly against cancer stem cells, these effects are significantly exerted. Furthermore, cancer stem cells can be easily detected and the site of the cancer stem cells can be accurately determined. More specifically, the present invention provides a cancer stem-cell detection probe.

DESCRIPTION OF EMBODIMENTS

Now, embodiments of the present invention will be described below.

A cancer cell inhibitory drug of the present invention, particularly, a cancer stem-cell inhibitory drug which is selectively taken into cancer cells, particularly, into cancer stem cells, thereby inhibiting cancer stem cells, and a cancer stem-cell detection probe will be described; however, the present invention is not limited to these.

Cancer Cell Inhibitory Drug

The cancer cell inhibitory drug refers to a composition having functions of suppressing growth, cellular division, metastasis and function of cancer cells and killing cancer cells. Furthermore, cancer cells can be detected and observed by measuring luminescence of the compound of the present invention.

A compound according to the present invention contains a compound represented by general formula (1).

Regarding compound represented by general formula (1)

General formula (1)

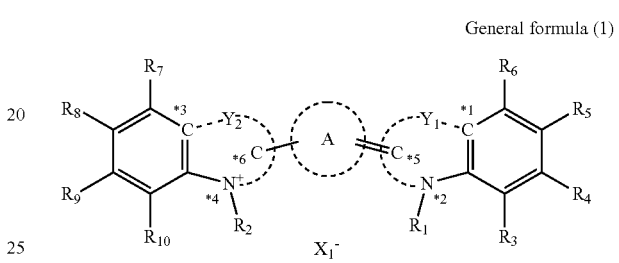

In general formula (1), $R_1$ and $R_2$ each independently represent an alkyl group, a carboxylalkyl group, an alkoxycarbonylalkyl group or an alkylcarbonyloxyalkyl group; $R_3$ to $R_{10}$ each independently represent a hydrogen atom, an alkyl group, an aryl group, an alkoxy group, a halogen atom, an alkoxysulfonyl group, a N-alkylsulfamoyl group, an alkyloxycarbonyl group, a carbamoyl group or a N-alkylcarbamoyl group; $R_3$ and $R_4$, $R_5$ and $R_6$, $R_7$ and $R_8$, and $R_9$ and $R_{10}$ may be each independently cyclized to form a benzene ring; $X_1^-$ represents an anionic group; $Y_1$ is a group including

*1, *2 and *5, and represents any one of the followings:

*1-S-*5-*2 (exemplified in compounds 1 to 12, 29, 39 and 42),

*1-O-*5-*2 (exemplified in compounds 13 to 19, 23, 28, 33, 38, 41, 44, 56 and 57),

*1-C(—$R_{11}$,—$R_{12}$)-*5-*2 (exemplified in compounds 20 to 22, 24 to 27, 30 to 32, 37, 40, 43, 49 to 55 and 58), and

*1-*5-CH=CH-*2 (exemplified in compounds 34 to 36 and 45 to 48), where $R_{11}$ and $R_{12}$ each independently represent an alkyl group, $R_{11}$ and $R_{12}$ may bind together to form a ring;

$Y_2$ is a group including *3, *4 and *6 and represents any one of the followings:

*4=*6-S-*3 (exemplified in compounds 1 to 12, 29, 34, 39 and 42),

*4=*6-O-*3 (exemplified in compounds 13 to 19, 23, 28, 33, 35, 38, 41, 44, 56 and 57),

*4=*6-C(—$R_{51}$, —$R_{52}$)-*3 (exemplified in compounds 20 to 22, 24 to 27, 30 to 32, 36, 37, 40, 43, 49 to 55 and 58),

*4=*6-CH=CH-*3 (exemplified in compounds 45, 47 and 48) and

*4=CH—CH=*6-*3 (exemplified in compound 46), where $R_{51}$ and $R_{52}$ each independently represent an alkyl group and $R_{51}$ and $R_{52}$ may bind together to form a ring; and a group including A to carbon atoms represented by *5 and *6 is represented by general formula (2) or (3):

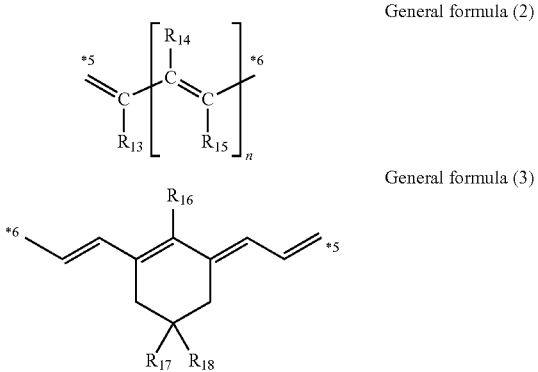

General formula (2)

General formula (3)

In general formula (2), $R_{13}$ to $R_{15}$ each independently represent a hydrogen atom, an alkyl group or an aryl group; and n represents an integer of 0 to 2, in general formula (3), $R_{16}$ represents a hydrogen atom, a phenyl group, a thiol group, an alkoxy group, an aryloxy group or a halogen atom; and $R_{17}$ and $R_{18}$ each independently represent a hydrogen atom, an alkyl group or an alkyloxycarbonyl group.

In general formula (1), examples of the alkyl group represented by $R_1$ and $R_2$ include, but are not particularly limited to, a methyl group, an ethyl group, a propyl group, a butyl group, a pentyl group and a hexyl group.

In general formula (1), examples of the carboxylalkyl group represented by $R_1$ and $R_2$ include, but are not particularly limited to, a carboxylmethyl group, a carboxylethyl group and a carboxylpropyl group.

In general formula (1), examples of the alkoxycarbonylalkyl group represented by $R_1$ and $R_2$ include, but are not particularly limited to, a methoxycarbonylmethyl group, a methoxycarbonylethyl group, an ethoxycarbonylethyl group, a butoxycarbonylethyl group and a methoxycarbonylpropyl group; and examples of the alkylcarbonyloxyalkyl group include, but are not particularly limited to, a methylcarbonyloxymethyl group, an ethylcarbonyloxymethyl group, an ethylcarbonyloxyethyl group, an ethylcarbonyloxybutyl group and a propylcarbonyloxymethyl group.

In general formula (1), examples of the alkyl groups represented by $R_3$ to $R_{10}$ include, but are not particularly limited to, a methyl group, an ethyl group, a propyl group, a butyl group, a pentyl group and a hexyl group.

In general formula (1), examples of the aryl groups represented by $R_3$ to $R_{10}$ include, but are not particularly limited to, a phenyl group, a 2-bromophenyl group, a 3-bromophenyl group, a 4-bromophenyl group, a 2-methoxyphenyl group, a 3-methoxyphenyl group, a 4-methoxyphenyl group, a 2-thiomethylphenyl group, a 3-thiomethylphenyl group, a 4-thiomethylphenyl group and a naphthyl group.

In general formula (1), examples of the alkoxy groups represented by $R_3$ to $R_{10}$ include, but are not particularly limited to, a methoxy group, an ethoxy group, a propoxy group and a butoxy group.

In general formula (1), examples of the halogen atoms represented by $R_3$ to $R_{10}$ include a fluorine atom, a chlorine atom, a bromine atom and an iodine atom.

In general formula (1), examples of the alkoxysulfonyl groups represented by $R_3$ to $R_{10}$ include, but are not particularly limited to, a methoxysulfonyl group and an ethoxysulfonyl group.

In general formula (1), examples of the N-alkylsulfamoyl groups represented by $R_3$ to $R_{10}$ include, but are not particularly limited to, a N-methylsulfamoyl group, a N-ethylsulfamoyl group, a N,N-dimethylsulfamoyl group and a N,N-diethylsulfamoyl group.

In general formula (1), examples of the alkyloxycarbonyl groups represented by $R_3$ to $R_{10}$ include, but are not particularly limited to, a methyloxycarbonyl group, an ethyloxycarbonyl group, a propyloxycarbonyl group and a butyloxycarbonyl group.

In general formula (1), examples of the N-alkylcarbamoyl groups represented by $R_3$ to $R_{10}$ include, but are not particularly limited to, a N-methylcarbamoyl group, a N-ethylcarbamoyl group, a N,N-dimethylcarbamoyl group and a N,N-diethylcarbamoyl group.

$R_3$ to $R_{10}$ in general formula (1) each independently represent preferably a hydrogen atom, a halogen atom, a phenyl group or an alkoxy group, and more preferably a hydrogen atom or a phenyl group.

In general formula (1), examples of the anionic group represented by $X_1^-$ include, but are not particularly limited to, a chloride ion, a bromide ion, an iodide ion, a sulfate ion, a nitrate ion, a methanesulfonate ion, a p-toluenesulfonate ion, a tetrafluoroborate ion and a hexafluorophosphate ion.

In general formula (1), examples of the alkyl groups represented by $R_{11}$, $R_{12}$, $R_{51}$ and $R_{52}$ in $Y_1$ and $Y_2$ include, but are not particularly limited to, a methyl group, an ethyl group, a propyl group, a butyl group, a pentyl group, a hexyl group and a 2-ethylhexyl group. $R_{11}$ and $R_{12}$ are favorably the same; however they may differ. $R_{51}$ and $R_{52}$ are favorably the same; however they may differ.

In general formula (1), $R_{11}$ and $R_{12}$ or $R_{51}$ and $R_{52}$ may bind together to form an aliphatic ring such as a cyclohexane ring and a cyclopentane ring.

In general formula (2), examples of the alkyl groups represented by $R_{13}$ to $R_{15}$ include, but are not particularly limited to, a methyl group, an ethyl group, a propyl group, a butyl group, a pentyl group and a hexyl group.

In general formula (2), examples of the aryl groups represented by $R_{13}$ to $R_{15}$ include, but are not particularly limited to, a phenyl group, a 2-bromophenyl group, a 3-bromophenyl group, a 4-bromophenyl group, a 2-methoxyphenyl group, a 3-methoxyphenyl group, a 4-methoxyphenyl group, a 2-thiomethylphenyl group, a 3-thiomethylphenyl group and a 4-thiomethylphenyl group.

In general formula (3), examples of the thiol group represented by $R_{16}$ include a methanethiol group, a butanethiol group and a benzenethiol group. Alternatively, the thiol group represented by $R_{16}$ may be a phenylthio group.

In general formula (3), examples of the alkoxy group represented by $R_{16}$ include a methoxy group, an ethoxy group, a propoxy group and a butoxy group.

In general formula (3), examples of the aryloxy group represented by $R_{16}$ include a phenoxy group and a phenoxy group which may have a substituent.

In general formula (3), examples of the halogen atoms represented by $R_{16}$ include a fluorine atom, a chlorine atom, a bromine atom and an iodine atom.

In general formula (3), examples of the alkyl groups represented by $R_{17}$ and $R_{18}$ include, but are not particularly limited to, a methyl group, an ethyl group, a propyl group, a butyl group, a pentyl group and a hexyl group.

In general formula (3), examples of the alkyloxycarbonyl groups represented by $R_{17}$ and $R_{18}$ include, but are not particularly limited to, a methyloxycarbonyl group, an ethyloxycarbonyl group, a propyloxycarbonyl group and a butyloxycarbonyl group.

Regarding compound represented by general formula (4)
As a favorable compound of the present invention, a compound represented by general formula (3) can be mentioned.

General formula (4)

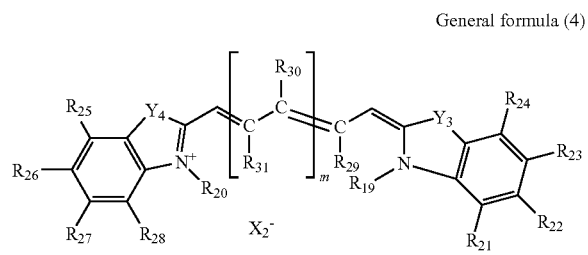

In general formula (4), $R_{19}$ and $R_{20}$ each independently represent an alkyl group, a carboxylalkyl group, an alkylcarbonyloxyalkyl group or an alkoxycarbonylalkyl group; and $R_{21}$ to $R_{28}$ each independently represent a hydrogen atom, an alkyl group, an aryl group, an alkoxy group, a halogen atom, an alkoxysulfonyl group, a N-alkylsulfamoyl group, an alkyloxycarbonyl group or a N-alkylcarbamoyl group. $R_{21}$ and $R_{22}$, $R_{23}$ and $R_{24}$, $R_{25}$ and $R_{26}$ and $R_{27}$ and $R_{28}$ may be each independently cyclized to form a benzene ring; $R_{29}$ to $R_{31}$ each independently represent a hydrogen atom, an alkyl group or an aryl group; and m represents an integer of 0 to 2. $X_2^-$ represents an anionic group; and $Y_3$ and $Y_4$ each independently represent an oxygen atom, a sulfur atom or an alkylene group and the alkylene group may have a substituent being alkyl group. If the alkylene group has two or more substituents being alkyl groups, they may bind together to form an aliphatic ring.

In general formula (4), examples of the alkyl group represented by $R_{19}$ and $R_{20}$ include, but are not particularly limited to, a methyl group, an ethyl group, a propyl group, a butyl group, a pentyl group and a hexyl group.

In general formula (4), examples of the carboxylalkyl group represented by $R_{19}$ and $R_{20}$ include, but are not particularly limited to, a carboxylmethyl group, a carboxylethyl group and a carboxylpropyl group.

In general formula (4), examples of the alkoxycarbonylalkyl group represented by $R_{19}$ and $R_{20}$ include, but are not particularly limited to, a methoxycarbonylmethyl group, a methoxycarbonylethyl group, an ethoxycarbonylethyl group, a butoxycarbonylethyl group and a methoxycarbonylpropyl group.

Examples of the alkylcarbonyloxyalkyl group include, but are not particularly limited to, a methylcarbonyloxymethyl group, an ethylcarbonyloxymethyl group, an ethylcarbonyloxyethyl group, an ethylcarbonyloxybutyl group and a propylcarbonyloxymethyl group.

In general formula (4), examples of the alkyl groups represented by $R_{21}$ to $R_{28}$ include, but are not particularly limited to, a methyl group, an ethyl group, a propyl group, a butyl group, a pentyl group and a hexyl group.

In general formula (4), examples of the aryl groups represented by $R_{21}$ to $R_{28}$ include, but are not particularly limited to, a phenyl group, a 2-bromophenyl group, a 3-bromophenyl group, a 4-bromophenyl group, a 2-methoxyphenyl group, a 3-methoxyphenyl group, a 4-methoxyphenyl group, a 2-thiomethylphenyl group, a 3-thiomethylphenyl group, a 4-thiomethylphenyl group and a naphthyl group.

In general formula (4), examples of the alkoxy groups represented by $R_{21}$ to $R_{28}$ include, but are not particularly limited to, a methoxy group, an ethoxy group, a propoxy group and a butoxy group.

In general formula (4), examples of the halogen atoms represented by $R_{21}$ to $R_{28}$ include a fluorine atom, a chlorine atom, a bromine atom and an iodine atom.

In general formula (4), examples of the alkoxysulfonyl groups represented by $R_{21}$ to $R_{28}$ include, but are not particularly limited to, a methoxysulfonyl group and an ethoxysulfonyl group.

In general formula (4), examples of the N-alkylsulfamoyl groups represented by $R_{21}$ to $R_{28}$ include, but are not particularly limited to, a N-methylsulfamoyl group, a N-ethylsulfamoyl group, a N,N-dimethylsulfamoyl group and a N,N-diethylsulfamoyl group.

In general formula (4), examples of the alkyloxycarbonyl groups represented by $R_{21}$ to $R_{28}$ include, but are not particularly limited to, a methyloxycarbonyl group, an ethyloxycarbonyl group, a propyloxycarbonyl group and a butyloxycarbonyl group.

In general formula (4), examples of the N-alkylcarbamoyl groups represented by $R_{21}$ to $R_{28}$ include, but are not particularly limited to, a N-methylcarbamoyl group, a N-ethylcarbamoyl group, a N,N-dimethylcarbamoyl group and a N,N-diethylcarbamoyl group.

$R_{21}$ to $R_{28}$ in general formula (4) each independently represent preferably a hydrogen atom, a halogen atom, a phenyl group or an alkoxy group, and more preferably a hydrogen atom or a phenyl group.

In general formula (4), examples of the alkyl groups represented by $R_{29}$ to $R_{31}$ include, but are not particularly limited to, a methyl group, an ethyl group, a propyl group, a butyl group, a pentyl group and a hexyl group.

In general formula (4), examples of the aryl group represented by $R_{29}$ to $R_{31}$ include, but are not particularly limited to, a phenyl group, a 2-bromophenyl group, a 3-bromophenyl group, a 4-bromophenyl group, a 2-methoxyphenyl group, a 3-methoxyphenyl group, a 4-methoxyphenyl group, a 2-thiomethylphenyl group, a 3-thiomethylphenyl group and a 4-thiomethylphenyl group.

In general formula (4), examples of the anionic group represented by $X_2^-$ include, but are not particularly limited to, a chloride ion, a bromide ion, an iodide ion, a sulfate ion, a nitrate ion, a methanesulfonate ion, a p-toluenesulfonate ion, a tetrafluoroborate ion and a hexafluorophosphate ion.

In general formula (4), $Y_3$ and $Y_4$ each independently represent an oxygen atom, a sulfur atom or an alkylene group and the alkylene group may have a substituent being alkyl group. If the alkylene group has two or more substituents being alkyl groups, they may bind together to form an aliphatic ring.

Examples of the alkylene group herein include, but are not particularly limited to, a methylene group, an ethylene group, a propylene group, a butylene group, a pentylene group, a hexylene group and a 2-ethylhexylene group. Examples of the aliphatic ring to be formed include, but are not particularly limited to, a cyclohexane ring and a cyclopentane ring.

The compounds represented by general formula (4) in the present invention are mostly commercially available and can be purchased and also synthesized in the same manner as in known methods (for example, NPL-3).

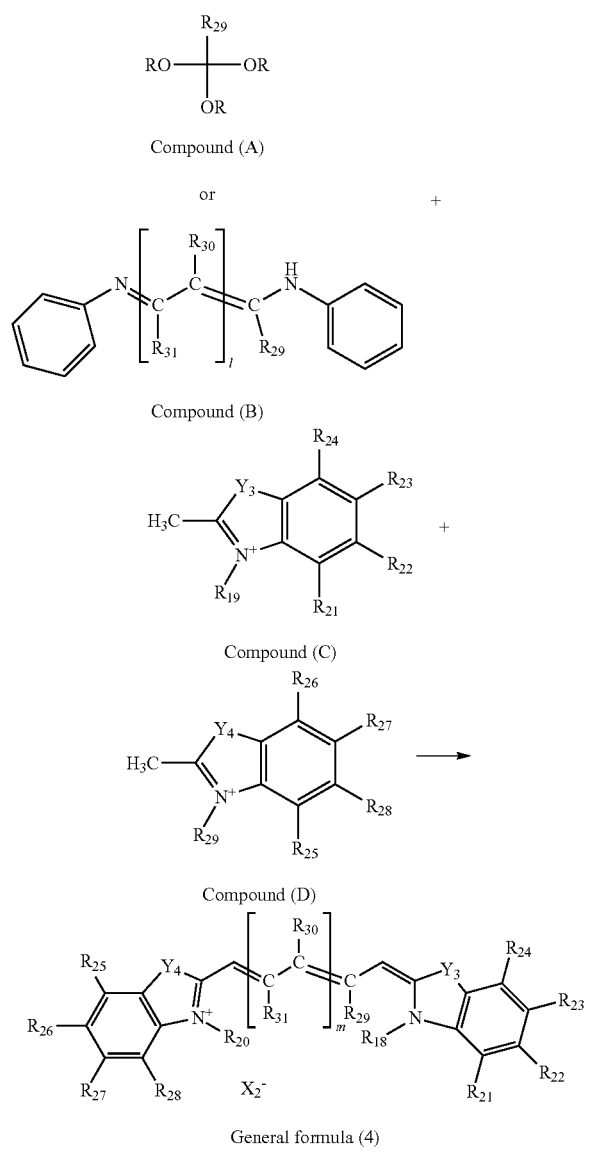

Compound (A)

or

Compound (B)

Compound (C)

Compound (D)

General formula (4)

m = 0

In the above compounds (A) to (D), $R_{19}$ to $R_{31}$, $X_2^-$, $Y_3$, and $Y_4$ are the same as defined in $R_{19}$ to $R_{31}$, $X_2^-$, $Y_3$ and $Y_4$ in compounds (A) to (D) in general formula (4). Furthermore, R in compound (A) represents an alkyl group such as a methyl group and an ethyl group.

More specifically, a compound represented by general formula (4) where m represents 0 is obtained by coupling compound (A), compound (C) and compound (D). A compound represented by general formula (4) where m represents 0 to 2 is obtained by coupling compound (B), compound (C) and compound (D).

Examples of the coupling method are not particularly limited. For example, a method of using compound (A) where m represents 0 will be described below as an embodiment.

The use amount of compound (C) in a coupling step relative to compound (A) (1 mole) is 0.1 to 1.2 times by mole, preferably 0.5 to 1.1 times by mole, and more preferably 0.8 to 1.0 times by mole.

The use amount of compound (D) in a coupling step relative to compound (A) (1 mole) is 0.1 to 2 times by mole, preferably 0.5 to 1.5 times by mole, and more preferably 0.8 to 1.2 times by mole.

The compound (C) and compound (D), which are not limited, may be the same or different; however, they are preferably the same compounds in view of process. The use amount of compound (C) and compound (D) relative to compound (A) (1 mole) when they are the same compounds, is 0.1 to 3 times by mole, preferably 0.5 to 2 times by mole, and more preferably 0.8 to 1.5 times by mole.

The coupling step can be performed in the absence of a solvent; however, it is favorably performed in the presence of a solvent. The solvent is not particularly limited as long as it is not involved in a reaction. Examples of the solvent include ester solvents such as methyl acetate, ethyl acetate, isopropyl acetate and butyl acetate; nitrile solvents such as acetonitrile, propionitrile and benzonitrile; aromatic solvents such as benzene, toluene, xylene, ethylbenzene, chlorobenzene and mesitylene; ether solvents such as diisopropyl ether, methyl-tert-butyl ether and tetrahydrofuran; alcohol solvents such as methanol, ethanol, n-propyl alcohol, iso-propyl alcohol, butyl alcohol and diethylene glycol; ketone solvents such as acetone and methylethyl ketone; dimethylformamide (DMF), dimethylsulfoxide (DMSO), water and acetic acid. Preferably, alcohol solvents such as methanol, ethanol, n-propyl alcohol, iso-propyl alcohol, butyl alcohol and diethylene glycol, water and acetic acid, and more preferably e.g., ethanol, iso-propyl alcohol and diethylene glycol and acetic acid are mentioned. Furthermore, two or more types of solvents can be used in combination and the mixing ratio of solvents used in combination can be determined at discretion.

The use amount of reaction solvent in the coupling step relative to compound (A) falls within the range of 0.1 to 1000 times by weight, preferably 0.5 to 500 times by weight, and more preferably 1.0 to 150 times by weight.

The reaction temperature in the coupling step falls within the range of −80 to 250° C., preferably −20 to 200° C., and more preferably 10 to 170° C. The reaction is generally completed within 24 hours.

In the coupling step, if an acid or a base is added as necessary, the reaction swiftly proceeds. The acid to be used is not particularly limited. Examples of the acid include inorganic acids such as hydrochloric acid, sulfuric acid and phosphoric acid; organic acids such as p-toluenesulfonic acid, formic acid, acetic acid, propionic acid, trifluoroacetic acid and acetic anhydride; strongly acidic ion exchange resins such as Amberlite (Rohm and Haas) and Amberlyst (Rohm and Haas); and inorganic acid salts such as ammonium formate and ammonium acetate. More preferably, an inorganic acid salt such as ammonium formate or ammonium acetate, and more preferably ammonium acetate is mentioned. The use amount of acid relative to compound (A) (1 mole) is 0.001 to 50 times by mole, preferably 0.01 to 10 times by mole, and more preferably 0.1 to 5 times by mole.

Specific examples of the base to be used in the coupling step include metal alkoxides such as potassium tert-butoxide, sodium tert-butoxide, sodium methoxide and sodium ethoxide; organic bases such as piperidine, pyridine, 2-methylpyridine, dimethylaminopyridine, diethylamine, triethylamine, isopropylethylamine, sodium acetate, potassium acetate, 1,8-diazabicyclo[5,4,0]undec-7-ene (hereinafter, simply referred to as DBU) and ammonium acetate; organic bases such as N-butyllithium and tert-butylmagnesium chloride; and inorganic bases such as sodium borohydride, metallic sodium, sodium hydride and sodium carbonate. Preferably, potassium tert-butoxide, sodium methoxide, sodium ethoxide, piperidine, dimethylaminopyridine, sodium acetate and ammonium acetate; and more preferably sodium methoxide, piperidine, sodium acetate and ammonium acetate are mentioned. The use amount of base as mentioned above relative to compound (A) (1 mole) is 0.1 to 20 times by mole, preferably 0.5 to 8 times by mole, and more preferably 1.0 to 4 times by mole.

After completion of the reaction, a reaction product is diluted with water or precipitated with an acid such as hydrochloric acid to obtain a compound represented by general formula (4).

To the obtained compound, isolation/purification methods generally used for organic compounds can be applied. For example, a reaction solution is acidified with an acid such as hydrochloric acid to precipitate a solid substance. The solid substrate is separated by filtration, neutralized with e.g., sodium hydroxide and concentrated to obtain a crude product. The crude product is further purified by e.g., recrystallization using e.g., acetone or methanol, or a column using silica gel. The crude product can be highly purified by employing these methods alone or in combination with two or more.

Regarding compound represented by general formula (5)
As a preferable compound of the present invention, a compound represented by general formula (5) can be mentioned.

General formula (5)

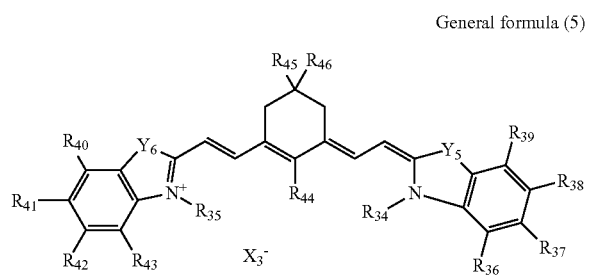

In general formula (5), $R_{34}$ and $R_{35}$ each independently represents an alkyl group, a carboxylalkyl group or an alkoxycarbonylalkyl group; and $R_{36}$ to $R_{43}$ each independently represent a hydrogen atom, an alkyl group, an aryl group, an alkoxy group, a halogen atom, an alkoxysulfonyl group, a N-alkylsulfamoyl group, an alkyloxycarbonyl group or a N-alkylcarbamoyl group. $R_{36}$ and $R_{37}$, $R_{38}$ and $R_{39}$, $R_{40}$ and $R_{41}$ and $R_{42}$ and $R_{43}$ may be each independently cyclized to form a benzene ring. $R_{44}$ represents a hydrogen atom, a phenyl group, a thiol group, an alkoxy group, an aryloxy group or a halogen atom; and $R_{45}$ and $R_{46}$ each independently represent a hydrogen atom, an alkyl group or an alkylcarbonyloxy group. $X_3^-$ represents an anionic group; and $Y_5$ and $Y_6$ each independently represent an oxygen atom, a sulfur atom or an alkylene group and the alkylene group may have substituents being alkyl groups which may bind together to form an aliphatic ring.

In general formula (5), examples of the alkyl group represented by $R_{34}$ and $R_{35}$ include, but are not particularly limited to, a methyl group, an ethyl group, a propyl group, a butyl group, a pentyl group and a hexyl group.

In general formula (5), examples of the carboxylalkyl group represented by $R_{34}$ and $R_{35}$ include, but are not particularly limited to, a carboxylmethyl group, a carboxylethyl group and a carboxylpropyl group.

In general formula (5), examples of the alkoxycarbonylalkyl group represented by $R_{34}$ and $R_{35}$ include, but are not particularly limited to, a methoxycarbonylmethyl group, a methoxycarbonylethyl group, an ethoxycarbonylethyl group, a butoxycarbonylethyl group and a methoxycarbonylpropyl group; and in general formula (5), examples of the alkyl groups represented by $R_{36}$ to $R_{43}$ include, but are not particularly limited to, a methyl group, an ethyl group, a propyl group, a butyl group, a pentyl group and a hexyl group.

In general formula (5), examples of the aryl groups represented by $R_{36}$ to $R_{43}$ include, but are not particularly limited to, a phenyl group, a 2-bromophenyl group, a 3-bromophenyl group, a 4-bromophenyl group, a 2-methoxyphenyl group, a 3-methoxyphenyl group, a 4-methoxyphenyl group, a 2-thiomethylphenyl group, a 3-thiomethylphenyl group, a 4-thiomethylphenyl group and a naphthyl group.

In general formula (5), examples of the alkoxy groups represented by $R_{36}$ to $R_{43}$ include, but are not particularly limited to, a methoxy group, an ethoxy group, a propoxy group and a butoxy group.

In general formula (5), examples of the halogen atoms represented by $R_{36}$ to $R_{43}$ include a fluorine atom, a chlorine atom, a bromine atom and an iodine atom.

In general formula (5), examples of the alkoxysulfonyl groups represented by $R_{36}$ to $R_{43}$ include, but are not particularly limited to, a methyl sulfonate group and an ethyl sulfonate group.

In general formula (5), examples of the alkylsulfamoyl groups represented by $R_{36}$ to $R_{43}$ include, but are not particularly limited to, a monomethylamide sulfonate group, a monoethylamide sulfonate group, a dimethylamide sulfonate group and a diethylamide sulfonate group.

In general formula (5), examples of the alkylcarbonyloxyalkyl groups represented by $R_{36}$ to $R_{43}$ include, but are not particularly limited to, a methylcarbonyloxymethyl group, an ethylcarbonyloxymethyl group, an ethylcarbonyloxyethyl group, an ethylcarbonyloxybutyl group and a propylcarbonyloxymethyl group.

In general formula (5), examples of the N-alkylcarbamoyl groups represented by $R_{36}$ to $R_{43}$ include, but are not particularly limited to, a N-methylcarbamoyl group, a N-ethylcarbamoyl group, a N,N-dimethylcarbamoyl group and a N,N-diethylcarbamoyl group.

$R_{36}$ to $R_{43}$ in general formula (5) each independently represent preferably a hydrogen atom, a halogen atom, a phenyl group or an alkoxy group, and more preferably a hydrogen atom or a phenyl group.

In general formula (5), examples of the thiol group represented by $R_{44}$ include a mercaptomethyl group, a mercaptobutyl group and a mercaptophenyl group. Alternatively, the thiol group represented by $R_{44}$ may be a phenylthio group.

In general formula (5), examples of the alkoxy group represented by $R_{44}$ include a methoxy group, an ethoxy group, a propoxy group and a butoxy group.

In general formula (5), examples of the aryloxy group represented by $R_{44}$ include a phenoxy group and a phenoxy group which may have a substituent.

In general formula (5), examples of the halogen atom represented by $R_{44}$ include a fluorine atom, a chlorine atom, a bromine atom and an iodine atom.

In general formula (5), examples of the alkyl group represented by $R_{45}$ and $R_{46}$ include, but are not particularly limited to, a methyl group, an ethyl group, a propyl group, a butyl group, a pentyl group and a hexyl group.

In general formula (5), examples of the alkyloxycarbonyl groups represented by $R_{45}$ and $R_{46}$ include, but are not particularly limited to, a methyloxycarbonyl group, an ethyloxycarbonyl group, a propyloxycarbonyl group and a butyloxycarbonyl group.

In general formula (5), examples of the anionic group represented by $X_3^-$ include, but are not particularly limited to, a chloride ion, a bromide ion, an iodide ion, a sulfate ion, a nitrate ion, a methanesulfonate ion, a p-toluenesulfonate ion, a tetrafluoroborate ion and a hexafluorophosphate ion.

In general formula (5), examples of the alkylene groups represented by $Y_5$ and $Y_6$ include, but are not particularly limited to, a methylene group, an ethylene group, a propylene group, a butylene group, a pentylene group, a hexylene group and a 2-ethylenehexyl group. Examples of the alkyl group serving as a substituent of an alkylene group include, but are not particularly limited to, a methyl group, an ethyl group, a propyl group and a butyl group.

The compounds represented by general formula (5) in the present invention are mostly commercially available and can be purchased and also synthesized in the same manner as in known methods (for example, NPL-4).

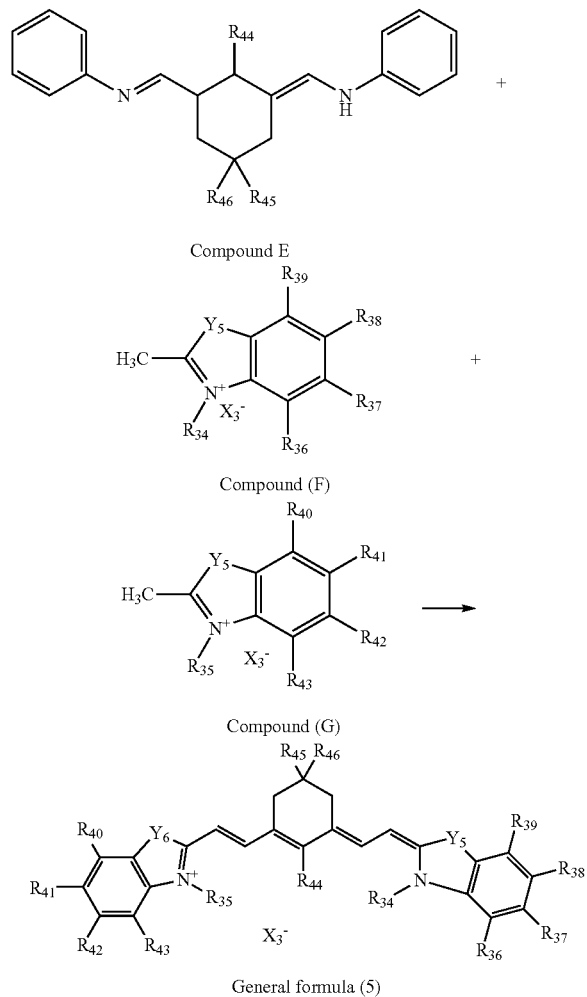

In compounds (E) to (G), $R_{35}$ to $R_{44}$, $X_3^-$, $Y_5$, and $Y_6$ are the same as defined in $R_{35}$ to $R_{44}$, $X_3^-$, $Y_5$, and $Y_6$ in compounds (E) to (G) in general formula (5).

More specifically, a compound represented by general formula (5) can be obtained by coupling compounds (E) to (G). Examples of the coupling method are not particularly limited. For example, a method described below is mentioned as an embodiment.

The use amount of compound (F) in a coupling step relative to compound (E) (1 mole) is 0.1 to 1.2 times by mole, preferably 0.5 to 1.1 times by mole, and more preferably 0.8 to 1.0 times by mole.

The use amount of compound (G) in a coupling step relative to compound (E) (1 mole) is 0.1 to 2 times by mole, preferably 0.5 to 1.5 times by mole, and more preferably 0.8 to 1.2 times by mole.

The compound (F) and compound (G), which are not limited, may be the same or different; however, they are preferably the same compounds in view of process. The use amount of compound (F) and compound (G) relative to compound (E) (1 mole) when they are the same compounds, is 0.1 to 3 times by mole, preferably 0.5 to 2 times by mole, and more preferably 0.8 to 1.5 times by mole.

The coupling step can be performed in the absence of a solvent; however, it is favorably performed in the presence of a solvent. The solvent is not particularly limited as long as it is not involved in a reaction. Examples of the solvent include ester solvents such as methyl acetate, ethyl acetate, isopropyl acetate and butyl acetate; nitrile solvents such as acetonitrile, propionitrile and benzonitrile; aromatic solvents such as benzene, toluene, xylene, ethylbenzene, chlorobenzene and mesitylene; ether solvents such as diisopropyl ether, methyl-tert-butyl ether and tetrahydrofuran; alcohol solvents such as methanol, ethanol, n-propyl alcohol, iso-propyl alcohol, butyl alcohol and diethylene glycol; ketone solvents such as acetone and methylethyl ketone; dimethylformamide (DMF), dimethylsulfoxide (DMSO), water and acetic acid. Preferably, alcohol solvents such as methanol, ethanol, n-propyl alcohol, iso-propyl alcohol, butyl alcohol and diethylene glycol, water and acetic acid, and more preferably e.g., ethanol, iso-propyl alcohol and diethylene glycol and acetic acid are mentioned. Furthermore, two or more types of solvents can be used in combination and the mixing ratio of solvents used in combination can be determined at discretion.

The use amount of reaction solvent in the coupling step relative to compound (E) falls within the range of 0.1 to 1000 times by weight, preferably 0.5 to 500 times by weight, and more preferably 1.0 to 150 times by weight.

The reaction temperature in the coupling step falls within the range of −80 to 250° C., preferably −20 to 200° C., and more preferably 10 to 170° C. The reaction is generally completed within 24 hours.

In the coupling step, if an acid or a base is added as necessary, the reaction swiftly proceeds. The acid to be used is not particularly limited. Examples of the acid include inorganic acids such as hydrochloric acid, sulfuric acid and phosphoric acid; organic acids such as p-toluenesulfonic acid, formic acid, acetic acid, propionic acid, trifluoroacetic acid and acetic anhydride; strongly acidic ion exchange resins such as Amberlite (Rohm and Haas) and Amberlyst (Rohm and Haas); and inorganic acid salts such as ammonium formate and ammonium acetate. More preferably, an inorganic acid salt such as ammonium formate or ammonium acetate, and more preferably ammonium acetate is mentioned. The use amount of acid relative to compound (E) (1 mole) is 0.001 to 50 times by mole, preferably 0.01 to 10 times by mole, and more preferably 0.1 to 5 times by mole.

Specific examples of the base to be used in the coupling step include metal alkoxides such as potassium tert-butoxide, sodium tert-butoxide, sodium methoxide and sodium ethoxide; organic bases such as piperidine, pyridine, 2-methylpyridine, dimethylaminopyridine, diethylamine, triethylamine, isopropylethylamine, sodium acetate, potassium acetate, 1,8-diazabicyclo[5,4,0]undec-7-ene (hereinafter, simply referred to as DBU) and ammonium acetate; organic bases such as N-butyllithium and tert-butylmagnesium chloride; and inorganic bases such as sodium borohydride, metallic sodium, sodium hydride and sodium carbonate. Preferably, potassium tert-butoxide, sodium methoxide, sodium ethoxide, piperidine, dimethylaminopyridine, sodium acetate and ammonium acetate; and more preferably sodium methoxide, piperidine, sodium acetate and ammonium acetate are mentioned. The use amount of base as mentioned above relative to compound (E) (1 mole) is 0.1 to 20 times by mole, preferably 0.5 to 8 times by mole, and more preferably 1.0 to 4 times by mole.

After completion of the reaction, a reaction product is diluted with water or precipitated with an acid such as hydrochloric acid to obtain a compound represented by general formula (5).

To the obtained compound, isolation/purification methods generally used for organic compounds can be applied. For example, a reaction solution is acidified with an acid such as hydrochloric acid to precipitate a solid substance. The solid substrate is separated by filtration, neutralized with e.g., sodium hydroxide and concentrated to obtain a crude product. Furthermore, the crude product is purified by e.g., recrystallization using e.g., acetone or methanol, or a column using silica gel. The crude product can be highly purified by employing these methods alone or in combination with two or more.

Regarding compound represented by general formula (6)
As a preferable compound of the present invention, a compound represented by general formula (6) can be mentioned.

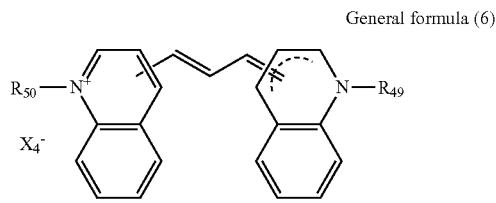

General formula (6)

In general formula (6), $R_{49}$ and $R_{50}$ each independently represent an alkyl group, a carboxylalkyl group, an alkylcarbonyloxyalkyl group or an alkoxycarbonylalkyl group. $X_4^-$ represents an anionic group.

In general formula (6), examples of the alkyl group represented by $R_{49}$ and $R_{50}$ include, but are not particularly limited to, a methyl group, an ethyl group, a propyl group, a butyl group, a pentyl group and a hexyl group.

In general formula (6), examples of the carboxylalkyl group represented by $R_{49}$ and $R_{50}$ include, but are not particularly limited to, a carboxylmethyl group, a carboxylethyl group and a carboxylpropyl group.

In general formula (6), examples of the alkoxycarbonylalkyl group represented by $R_{49}$ and $R_{50}$ include, but are not particularly limited to, a methoxycarbonylmethyl group, a methoxycarbonylethyl group, an ethoxycarbonylethyl group, a butoxycarbonylethyl group and a methoxycarbonylpropyl group; and examples of the alkylcarbonyloxyalkyl group include, but are not particularly limited to, a methylcarbonyloxymethyl group, an ethylcarbonyloxymethyl group, an ethylcarbonyloxyethyl group, an ethylcarbonyloxybutyl group and a propylcarbonyloxymethyl group.

In general formula (6), examples of the anionic group represented by $X_4^-$ include, but are not particularly limited to, a chloride ion, a bromide ion, an iodide ion, a sulfate ion, a nitrate ion and a methanesulfonate ion.

The compounds represented by general formula (6) in the present invention are mostly commercially available and can be purchased and also synthesized in the same manner as in known methods (for example, NPL-5).

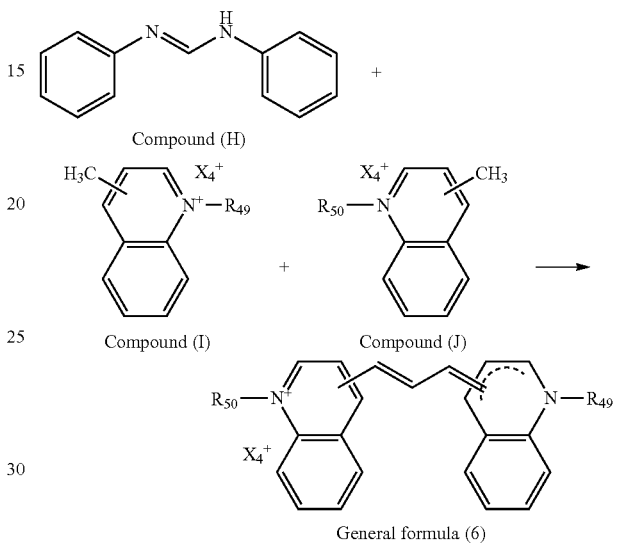

General formula (6)

In compounds (H) to (J), $R_{49}$, $R_{50}$ and $X_4^-$ are the same as defined in $R_{49}$, $R_{50}$ and $X_4^-$ in compounds (H) to (J) in general formula (6).

More specifically, a compound represented by general formula (6) can be obtained by coupling compounds (H) to (J). Examples of the coupling method is not particularly limited. For example, a method described below is mentioned as an embodiment.

The use amount of compound (I) in a coupling step relative to compound (H) (1 mole) is 0.1 to 1.2 times by mole, preferably 0.5 to 1.1 times by mole, and more preferably 0.8 to 1.0 times by mole.

The use amount of compound (J) in a coupling step relative to compound (H) (1 mole) is 0.1 to 2 times by mole, preferably 0.5 to 1.5 times by mole, and more preferably 0.8 to 1.2 times by mole.

The compound (I) and compound (J), which are not limited, may be the same or different; however, preferably the same compounds in view of process. The use amount of compound (I) and compound (J) relative to compound (H) (1 mole) when they are the same compounds, is 0.1 to 3 times by mole, preferably 0.5 to 2 times by mole, and more preferably 0.8 to 1.5 times by mole.

The coupling step can be performed in the absence of a solvent; however, it is favorably performed in the presence of a solvent. The solvent is not particularly limited as long as it is not involved in a reaction. Examples of the solvent include ester solvents such as methyl acetate, ethyl acetate, isopropyl acetate and butyl acetate; nitrile solvents such as acetonitrile, propionitrile and benzonitrile; aromatic solvents such as benzene, toluene, xylene, ethylbenzene, chlorobenzene and mesitylene; ether solvents such as diisopropyl ether, methyl-tert-butyl ether and tetrahydrofuran;

alcohol solvents such as methanol, ethanol, n-propyl alcohol, iso-propyl alcohol, butyl alcohol and diethylene glycol; ketone solvents such as acetone and methylethyl ketone; dimethylformamide (DMF), dimethylsulfoxide (DMSO), water and acetic acid. Preferably, alcohol solvents such as methanol, ethanol, n-propyl alcohol, iso-propyl alcohol, butyl alcohol and diethylene glycol, water and acetic acid, and more preferably e.g., ethanol, iso-propyl alcohol and diethylene glycol and acetic acid are mentioned. Furthermore, two or more types of solvents can be used in combination and the mixing ratio of solvents used in combination can be determined at discretion.

The use amount of reaction solvent in the coupling step relative to compound (H) falls within the range of 0.1 to 1000 times by weight, preferably 0.5 to 500 times by weight, and more preferably 1.0 to 150 times by weight.

The reaction temperature in the coupling step falls within the range of −80 to 250° C., preferably −20 to 200° C., and more preferably 10 to 170° C. The reaction is generally completed within 24 hours.

In the coupling step, if an acid or a base is added as necessary, the reaction swiftly proceeds. The acid to be used is not particularly limited. Examples of the acid include inorganic acids such as hydrochloric acid, sulfuric acid and phosphoric acid; organic acids such as p-toluenesulfonic acid, formic acid, acetic acid, propionic acid, trifluoroacetic acid and acetic anhydride; strongly acidic ion exchange resins such as Amberlite (Rohm and Haas) and Amberlyst (Rohm and Haas); and inorganic acid salts such as ammonium formate and ammonium acetate. More preferably, an inorganic acid salt such as ammonium formate or ammonium acetate, and more preferably ammonium acetate is mentioned. The use amount of acid relative to compound (H) (1 mole) is 0.001 to 50 times by mole, preferably 0.01 to 10 times by mole, and more preferably 0.1 to 5 times by mole.

Specific examples of the base to be used in the coupling step include metal alkoxides such as potassium tert-butoxide, sodium tert-butoxide, sodium methoxide and sodium ethoxide; organic bases such as piperidine, pyridine, 2-methylpyridine, dimethylaminopyridine, diethylamine, triethylamine, isopropylethylamine, sodium acetate, potassium acetate, 1,8-diazabicyclo[5,4,0]undec-7-ene (hereinafter, simply referred to as DBU) and ammonium acetate; organic bases such as N-butyllithium and tert-butylmagnesium chloride; and inorganic bases such as sodium borohydride, metallic sodium, sodium hydride and sodium carbonate. Preferably, potassium tert-butoxide, sodium methoxide, sodium ethoxide, piperidine, dimethylaminopyridine, sodium acetate and ammonium acetate; and more preferably sodium methoxide, piperidine, sodium acetate and ammonium acetate are mentioned. The use amount of base as mentioned above relative to compound (H) (1 mole) is 0.1 to 20 times by mole, preferably 0.5 to 8 times by mole, and more preferably 1.0 to 4 times by mole.

After completion of the reaction, a reaction product is diluted with water or precipitated with an acid such as hydrochloric acid to obtain a compound represented by general formula (6).

To the obtained compound, isolation/purification methods generally used for organic compounds can be applied. For example, a reaction solution is acidified with an acid such as hydrochloric acid to precipitate a solid substance. The solid substrate is separated by filtration, neutralized with e.g., sodium hydroxide and concentrated to obtain a crude product. Furthermore, the crude product is purified by e.g., recrystallization using e.g., acetone or methanol, or a column using silica gel. The crude product can be highly purified by employing these methods alone or in combination with two or more.

Now, compounds (1) to (60) will be shown below as preferable examples of the compounds according to the present invention; however, the present invention is not limited to the following examples.

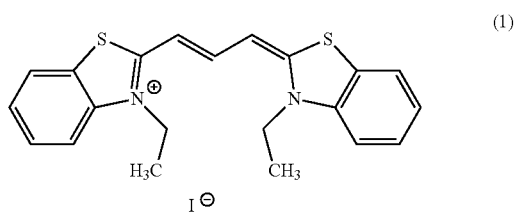

(1)

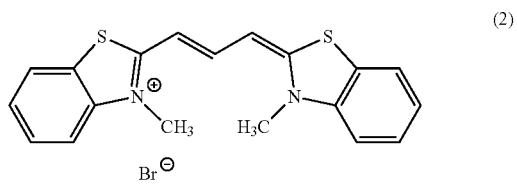

(2)

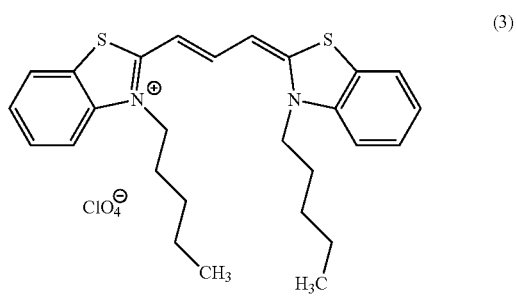

(3)

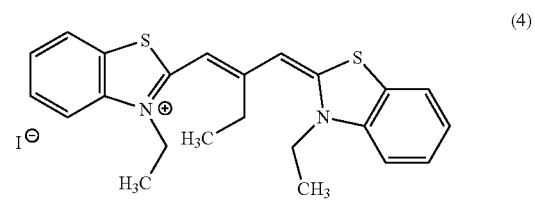

(4)

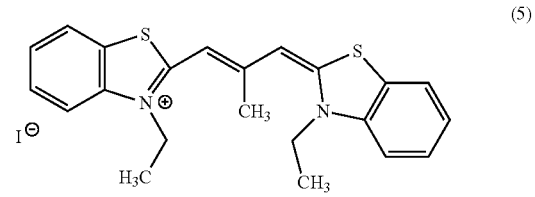

(5)

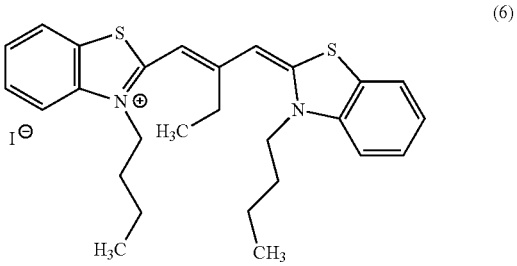

(6)

-continued
(7)
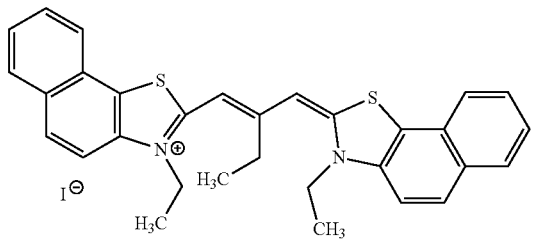
(8)
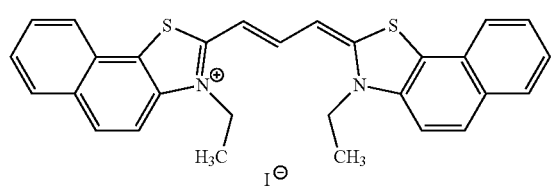
(9)
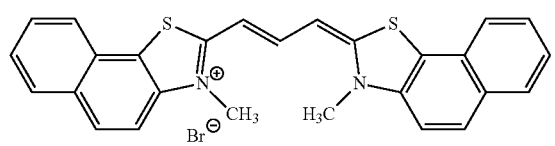
(10)
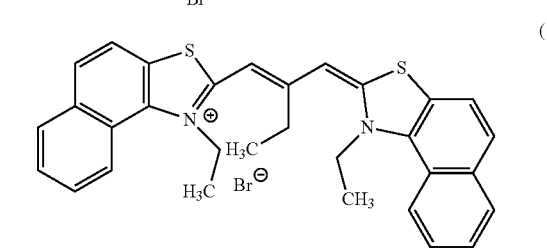
(11)
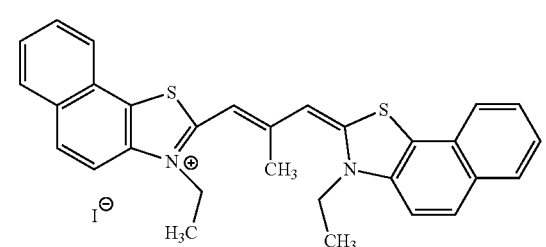
(12)
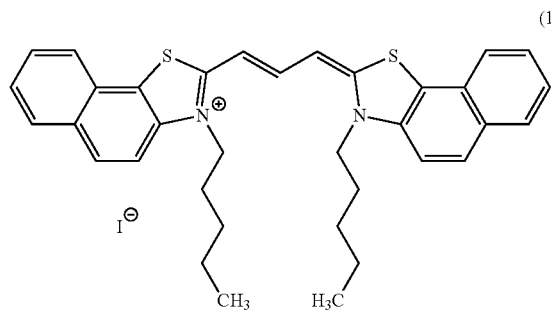
(13)
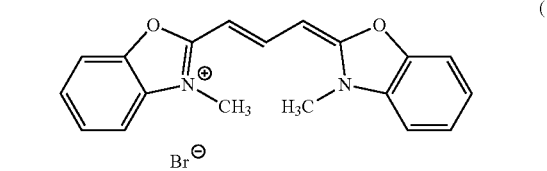
-continued
(14)
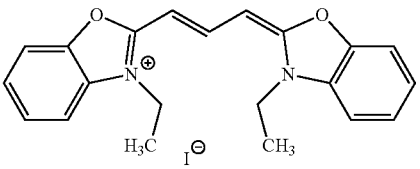
(15)
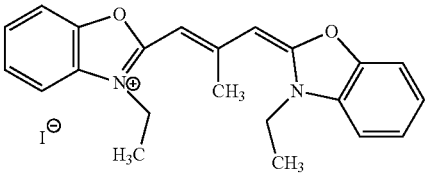
(16)
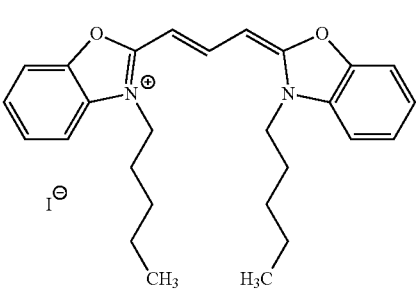
(17)
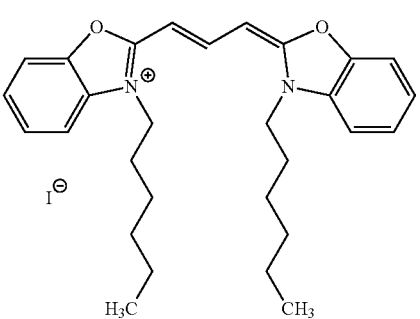
(18)
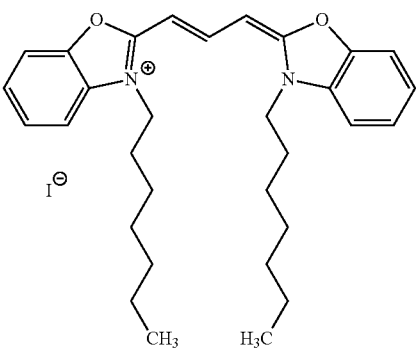
(19)
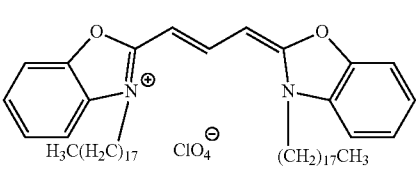

(20)
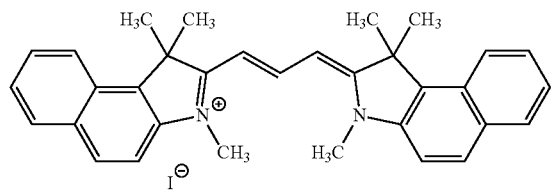
(21)
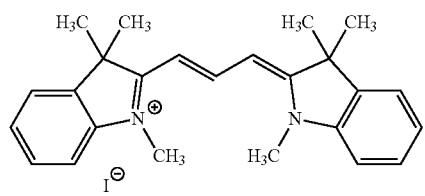
(22)
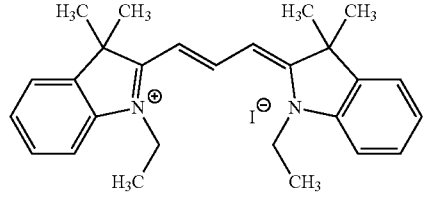
(23)
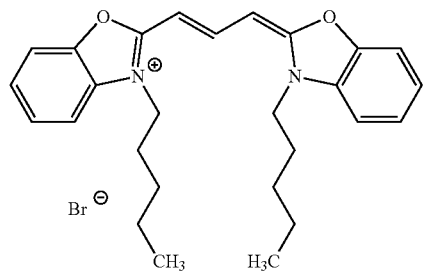
(24)
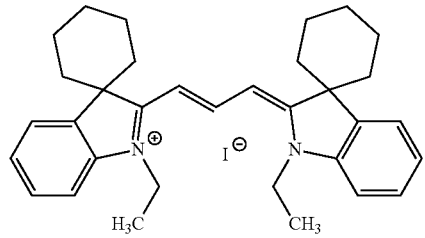
(25)
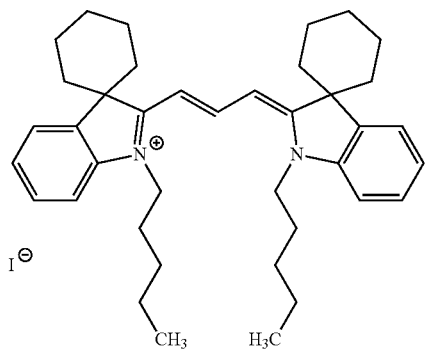
(26)
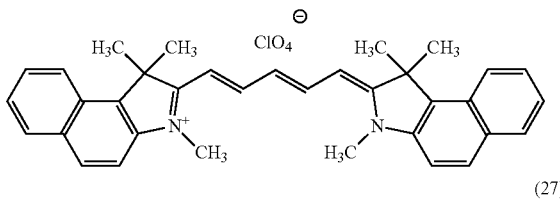
(27)
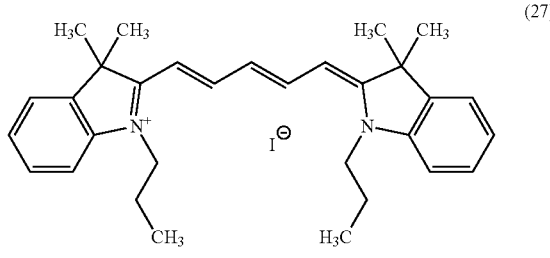
(28)
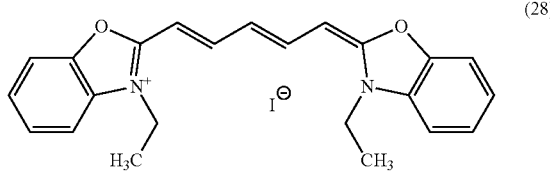
(29)
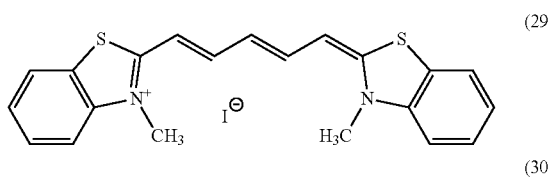
(30)
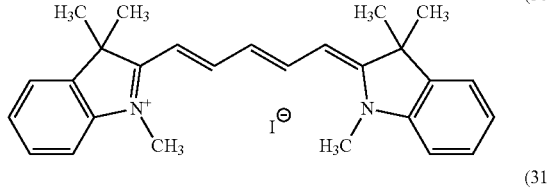
(31)
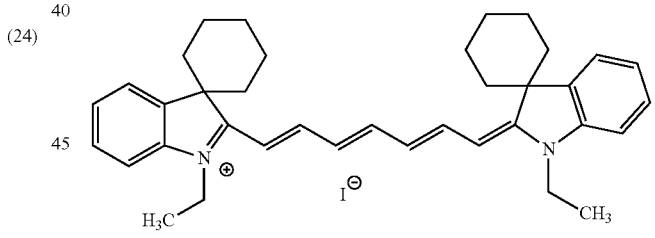
(32)
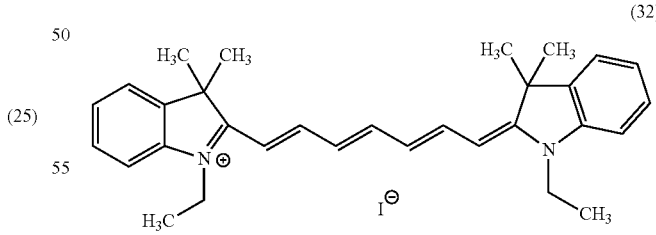
(33)
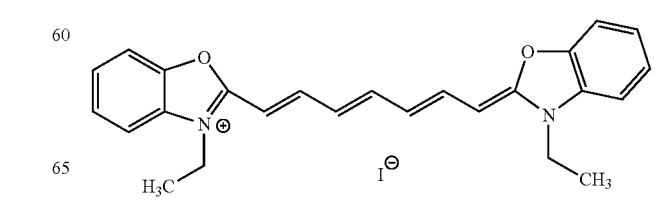

-continued
(34)
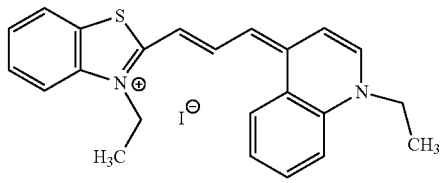
(35)
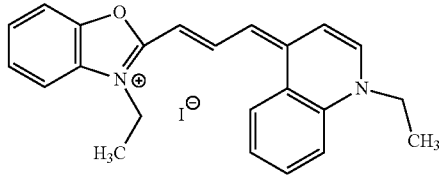
(36)
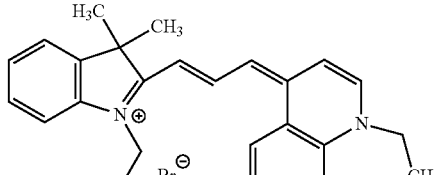
(37)
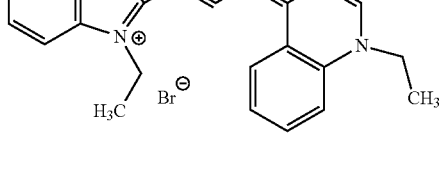
(38)
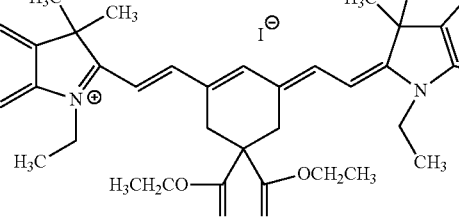
(39)
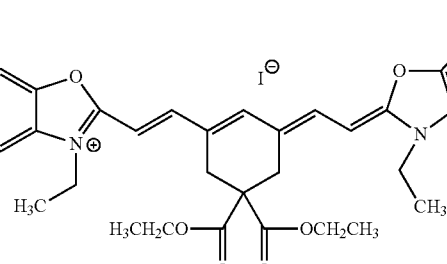
(40)
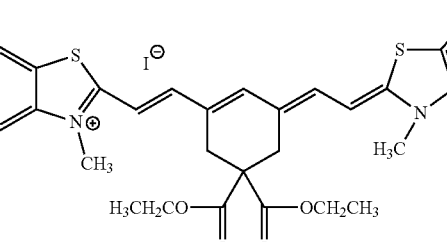
-continued
(41)
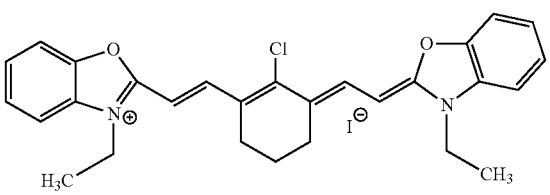
(42)
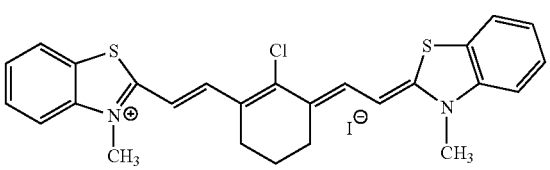
(43)
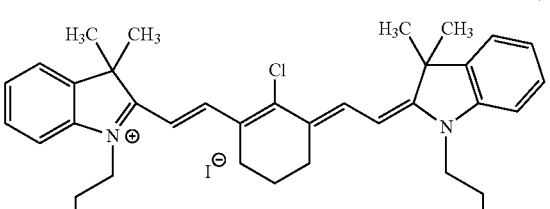
(44)
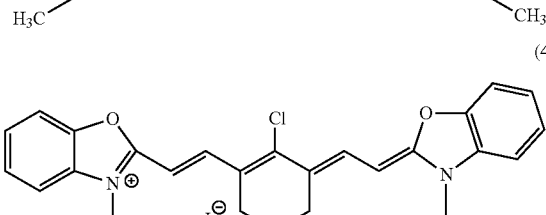
(45)
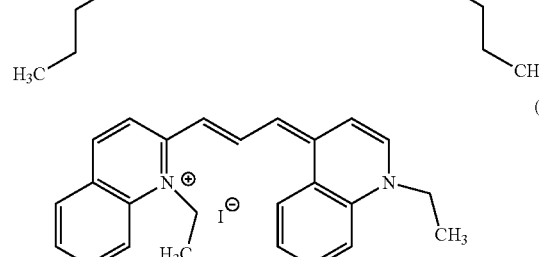
(46)
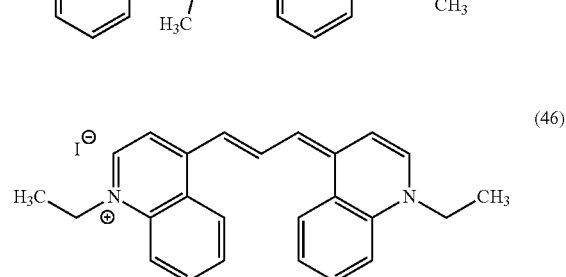
(47)
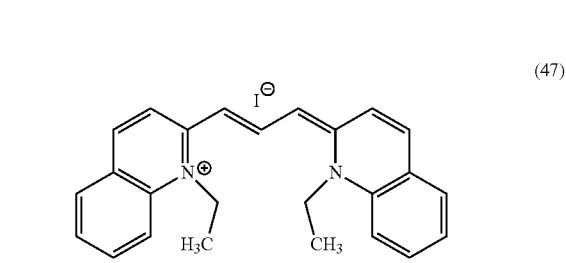

-continued
(48)
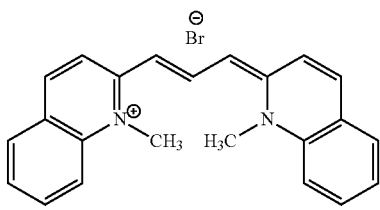
(49)
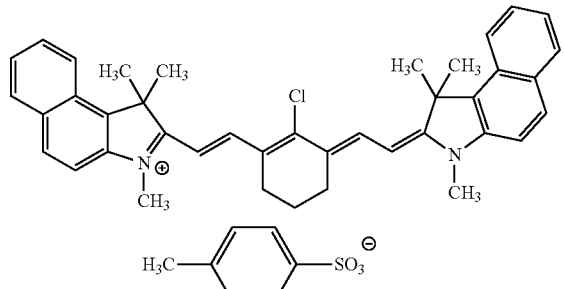
(50)
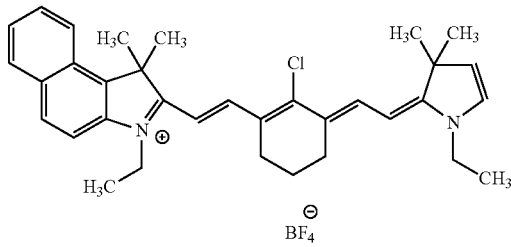
(51)
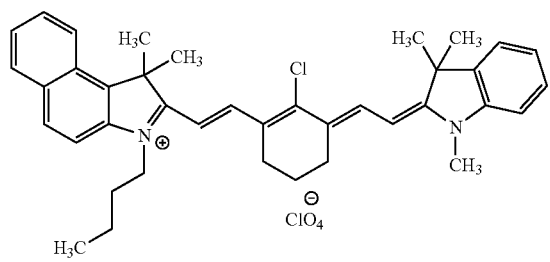
(52)
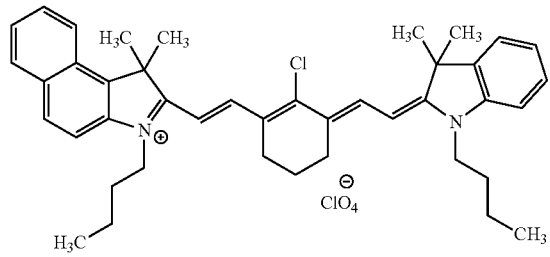
-continued
(53)
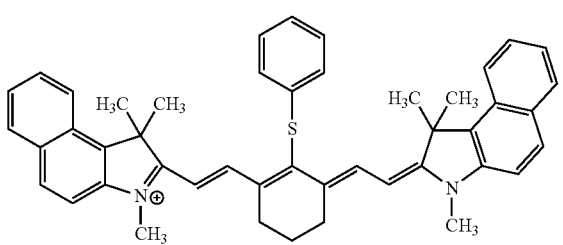
(54)
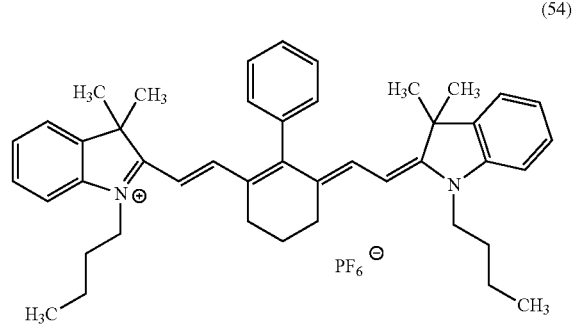
(55)
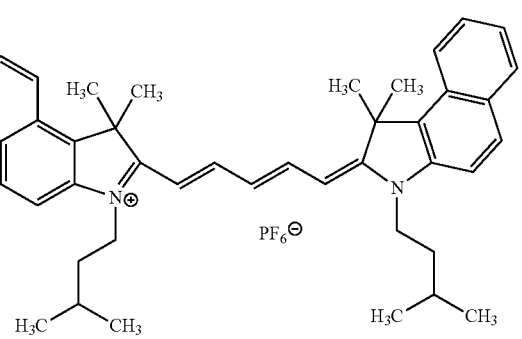
(56)
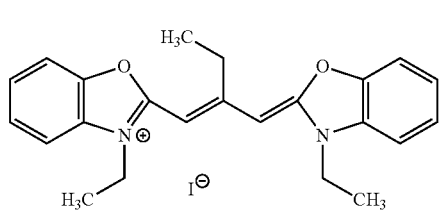
(57)
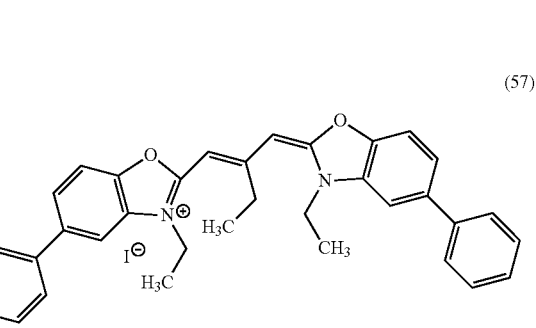

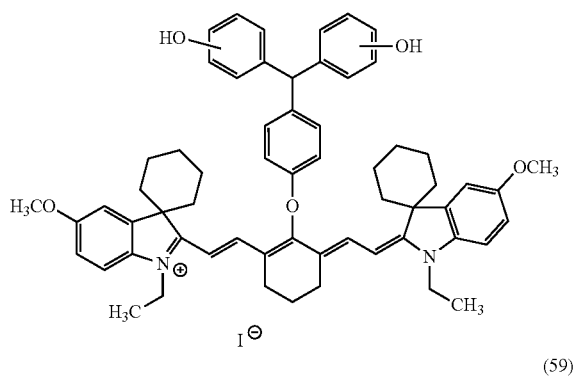

(58)

(59)

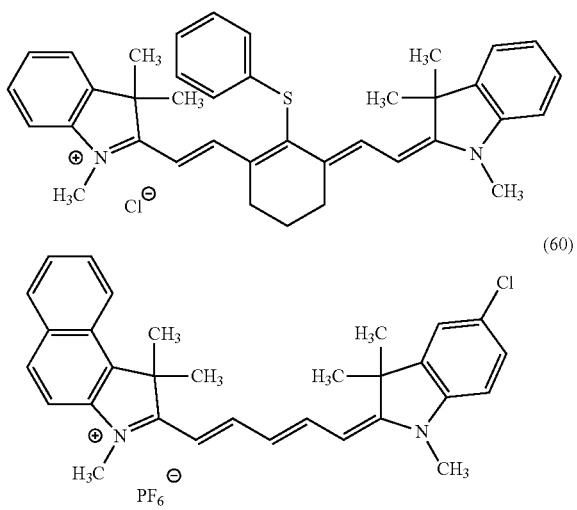

(60)

The compounds of the present invention are favorably emitted by light upon irradiation with excitation light of 350 to 800 nm in wavelength.

The compounds of the present invention is characterized in that growth suppression, cellular division suppression, metastasis suppression, functional inhibition and cytocidal action of cancer cells are mediated by taking a compound selectively into the cancer cells. Further, cancer cells can be detected and observed by measuring luminescence of the compound of the present invention.

The compounds of the present invention may be used alone or in combination with two types or more for cancer inhibition, and may be used in combination with a known anti-cancer drug(s).

In the present invention, an effect is selectively exerted particularly on cancer stem cells among cancer cells.

Cancer Stem Cells

In the specification, the cancer stem cells refer to cancer cells having properties of the stem cells. The stem cells refer to cells having two functions, i.e., self-replication ability and pluripotency (ability to differentiate into various types of cells).

Applicable Cancer

Examples of the cancer to be inhibited by the compound of the present invention include, but are not particularly limited to Examples of the cancers include breast cancer, brain tumor, stomach cancer, prostatic cancer, pancreatic cancer, lung cancer, large bowel cancer, small intestine cancer, colon cancer, rectal cancer, esophagus cancer, duodenal cancer, tongue cancer, pharyngeal cancer, liver cancer, endometrium cancer, uterine cervix cancer, renal cancer, bile duct cancer, ovarian cancer, bladder cancer, skin cancer, blood vessel cancer, salivary gland cancer, thyroid cancer, parathyroid gland cancer, nasal cavity cancer, paranasal sinus cancer, penile cancer, infant solid cancer, malignant lymphoma, malignant melanoma, retina sarcoma, testicular tumor, myeloma, sarcoma, blood vessel fibroma and leukemia. Preferably, e.g., pancreatic cancer, prostatic cancer and leukemia are mentioned. Particularly, applicable cancers may include cancer stem cells or cells originated from cancer stem cells.

Test Subject

Examples of the subject used in a test for checking whether a compound of the present invention suppresses a cancer or not include, but are not particularly limited to, vertebral animals including bony fish such as *Takifugu* (Japanese pufferfish), *Takifugu niphobles*, green spotted pufferfish (*Tetraodon nigroviridis*), killifish and zebra fish, amphibians such as *Xenopus*, birds such as fowl and quail, and mammalians such as human, monkey, chimpanzee, calf, horse, pig, dog, cat, mouse, rat, guinea pig, hamster and rabbit; small animals such as rat, mouse and hamster; and large animals such as goat, pig, dog, cat, calf and horse, monkey, chimpanzee and human. Favorably, e.g., human, mouse, rat, dog and cat are mentioned.

When a compound of the present invention is used as a medicinal drug, various types of dosage forms can be selected depending upon the administration route. Examples of dosage forms that can be used include liquid, syrup, fine granule, granule, tablet, capsule, pasting medicine and drug delivery system (DDS) such as liposome.

The administration method of a compound of the present invention is not limited and oral or parenteral administration may be used. Examples of the administration method that can be used include exposure to a living body (e.g., liquid); administration such as oral, intravascular (through e.g., a vein or an artery), peroral, sublingual, intrarectal, intraperitoneal, dermal, subcutaneous, intracutaneous, intravesical, tracheal (via bronchia), intraocular and intranasal administrations; and injection, spray and application into ear or the like.

A compound of the present invention, if necessary, may contain pharmacologically or pharmaceutically acceptable additives such as a moisturizer, a surface tension moderator, a thickener, a pH moderator, a pH buffer, a preservative, an antibacterial agent, a sweetening agent, a flavor, a solubilizer, a solubilizing agent, a coating agent and a binder.

The dose of the compound of the present invention is appropriately determined depending upon a purpose for therapy or prophylaxis, and conditions such as sexuality, age, weight of a test subject, an administration route, and degree of a disease.

Transplant Model Animal

Generally, it is difficult to monitor behavior of metastatic cancer by culturing cells. Thus, in the present invention, in order to monitor behavior of metastatic cancer, particularly, a transplant model animal can be used.

Examples of the cancer-cell transplant model animal applicable to the present invention include, but are not particularly limited to, vertebral animals including bony fish such as *Takifugu* (Japanese pufferfish), *Takifugu niphobles*, green spotted pufferfish (*Tetraodon nigroviridis*), killifish and zebra fish, amphibians such as *Xenopus*, birds such as fowl and quail, mammalians such as human, monkey, chimpanzee, calf, horse, pig, dog, cat, mouse, rat, guinea pig, hamster and rabbit, and birds such as fowl and quail; small animals such as rat, mouse and hamster; and large animals such as goat, pig, dog, cat, calf and horse, monkey and chimpanzee. Favorably, e.g., mouse, rat, dog and cat are mentioned.

Of these, e.g., immunodeficiency mice and rats, are often generally used in an initial study. In this case, it is necessary to maintain an environment by use of e.g., a clean room in the period (usually, at least 3 to 6 months) during which the study is carried out. In addition, extraordinary labor cost for management during this period is required.

For the reason, among these biological samples, zebra fish is particularly preferably used in view of cost and speed (usually at least a week). Zebra fish has been recently and already recognized as a third model animal which comes next to mice and rats in the United States and the United Kingdom. It has been elucidated that, the entire genomic sequence of zebra fish has a 80% homology to that of a human and the number of genes of zebra fish is virtually the same as that of a human. Furthermore, development and structure of major organs/tissues are mutually quite resembled. Since a process from differentiation of a fertilized egg to formation of each part (organ such as heart, liver, kidney and digestive tube) can be observed through a transparent body, it is particularly preferable to use zebra fish (the inside of which can be observed non-invasively) for screening as a model animal.

Furthermore, zebra fish lay about 200 or more fertilized eggs per time. Since zebra fish having the same genetic background are obtained, zebra fish is advantageous for screening.

The method for administering a compound of the present invention is not particularly limited; however, a cancer cell inhibitory drug may be suspended in the form of a complex with an appropriate surfactant or in the form of an emulsion in breeding water. Alternatively, the cancer cell inhibitory drug may be mixed in feed or food and orally or parenterally (e.g., injection) administered.

Cancer Stem Cell Detection Probe

Since the compound of the present invention can be used for selective detection of cancer stem cells, it can be suitably used as a cancer stem-cell detection probe. More specifically, the present invention encompasses a cancer cell detection probe.

The ratio of the compound of the present invention particularly taken into cancer stem cells among the cancer cells is large. Thus, cancer stem cells can be selectively detected. Detection and confirmation of behavior of cancer stem cells by the present invention can be carried out all in vitro, ex vivo or in vivo.

A method for detecting, by use of a compound of the present invention, which is not particularly limited as long as it has no effect upon cancer stem cells, is a method for capturing state and change of a biological sample as an image. For example, visible light, near infrared light or infrared light is applied to cancer stem cells and an image is visually observed by e.g., a camera or CCD, namely, visible light observation, near infrared light observation and infrared light observation are mentioned. Alternatively, observation by a laser microscope; fluorescence observation in which excitation light is applied to a biological sample from an excitation-light source and fluorescence emitted from the biological sample is observed by a fluorescent endoscope or the like; observation by a fluorescent microscope; observation by a fluorescent endoscope; observation by a confocal fluorescence microscope; or observation by a multiphoton excitation fluorescence microscope is mentioned. Alternatively, narrow-band light observation; colight interference tomogram observation (OCT) or observation by a soft X ray microscope is mentioned. Particularly, fluorescence observation is favorable.

The wavelength of light for exciting a compound of the present invention varies depending upon the compound represented by general formula (1) and the wavelength of the excitation light is not particularly limited as long as a cancer cell detection probe of the present invention efficiently emits fluorescent light.

The wavelength is preferably, 200 to 1010 nm, more preferably 400 to 900 nm, and more preferably 480 to 800 nm. When light within a near infrared region is used, the wavelength that is used is preferably 600 to 1000 nm, and more preferably 680 to 900 nm, which is also excellent in permeability through a living body.

The source of excitation light for exciting a compound of the present invention is not particularly limited and various types of laser light sources can be used. Examples of these laser light sources include a dye laser light source, a semiconductor laser light source, an ion laser light source, a fiber laser light source, a halogen lamp, a xenon lamp and a tungsten lamp. Alternatively, if various types of optical filters are used, a favorable excitation wavelength can be obtained and fluorescence alone can be detected.

As described above, in the state where a compound of the present invention present within cancer stem cells is allowed to emit light by applying excitation light to an individual biological organism, if the cancer stem cells can be photographed, a luminescent site can be easily detected. Furthermore, if an image in light field, which is obtained by applying visible light, is combined with a fluorescent image, which is obtained by applying excitation light, with the help of an image processing unit, cancer stem cells can be more specifically observed. Furthermore, if a confocal microscope is used, a sectional optical image can be favorably obtained. Furthermore, a multiphoton excitation fluorescence microscope, since it is highly permeable to a deep portion and a spatial resolution, is favorably used for observing inside a tissue.

EXAMPLES

Now, the present invention will be more specifically described below by way of Examples. These are specific Examples for further deep understanding of the present invention and should not be construed as limiting the invention.

Example 1

Production Examples of the compounds of the present invention will be shown.

Production of Compound (1)

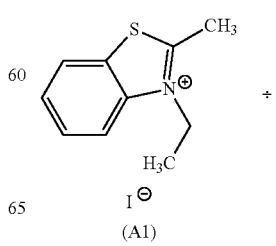

(A1)

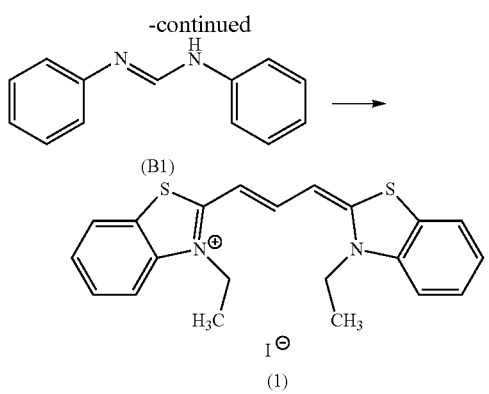

Under a nitrogen atmosphere, to a solution of compound (A1) (0.61 g (2.0 mmol)) in anhydrous acetic acid (10 mL), a compound (B1) (0.20 g (1.0 mmol)) and anhydrous sodium acetate (0.16 g (2.0 mmol)) were added and stirred at 100° C. for one hour. After completion of the reaction, while the reaction solution was cooled, saturated saline (100 mL) was gently added dropwise to cool the reaction solution to room temperature. Furthermore, the reaction solution was extracted twice with dichloromethane (50 mL) and dried over anhydrous sodium acetate. Thereafter, the organic layer was concentrated under reduced pressure. The residue was purified by silica gel chromatography and the purified product was recrystallized from diethyl ether to obtain the compound (1) (0.29 g (yield 59%)). The desired product was confirmed by $^1$H nuclear magnetic resonance spectroscopic analysis (ECA-400, manufactured by JEOL Ltd.) and LC/TOF MS (LC/MSD TOF, manufactured by Agilent Technologies).

Production of Compound (40)

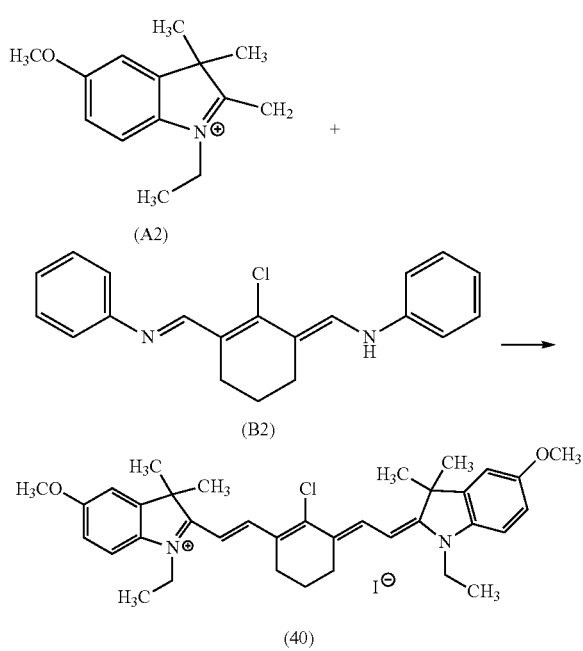

Under a nitrogen atmosphere, to a solution of compound (A2) (0.48 g (2.2 mmol)) in anhydrous acetic acid (10 mL), a compound (B2) (0.32 g (1.0 mmol)) and anhydrous sodium acetate (0.25 g (3.0 mmol)) were added and stirred at 100° C. for one hour. After completion of the reaction, while the reaction solution was cooled, saturated saline (100 mL) was gently added dropwise to cool the reaction solution to room temperature. Furthermore, the reaction solution was extracted twice with dichloromethane (50 mL) and dried over anhydrous sodium acetate. Thereafter, the organic layer was concentrated under reduced pressure. The residue was purified by silica gel chromatography and the purified product was recrystallized from diethyl ether to obtain the compound (40) (0.38 g (yield 54%)). The desired product was confirmed by $^1$H nuclear magnetic resonance spectroscopic analysis (ECA-400, manufactured by JEOL Ltd.) and LC/TOF MS (LC/MSD TOF, manufactured by Agilent Technologies).

Production of Compound (46)

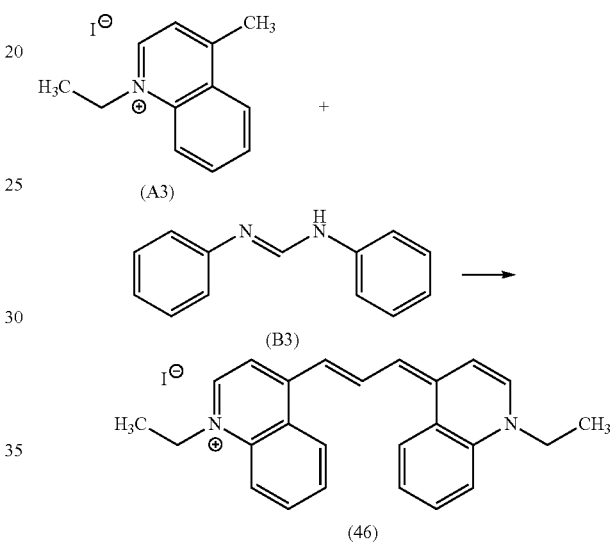

Under a nitrogen atmosphere, to a solution of compound (A3) (0.90 g (3.0 mmol)) in anhydrous acetic acid (15 mL), a compound (B3) (0.29 g (1.5 mmol)) and anhydrous sodium acetate (0.29 g (3.5 mmol)) were added and stirred at 100° C. for 1.5 hours. After completion of the reaction, while the reaction solution was cooled, saturated saline (100 mL) was gently added dropwise to cool the reaction solution to room temperature. Furthermore, the reaction solution was extracted twice with dichloromethane (50 mL) and dried over anhydrous sodium acetate. Thereafter, the organic layer was concentrated under reduced pressure. The residue was purified by silica gel chromatography and the purified product was recrystallized from diethyl ether to obtain the compound (46) (0.46 g (yield 64%)). The desired product was confirmed by $^1$H nuclear magnetic resonance spectroscopic analysis (ECA-400, manufactured by JEOL Ltd.) and LC/TOF MS (LC/MSD TOF, manufactured by Agilent Technologies).

Furthermore, commercially available products were purchased or 32 types of compounds shown in Table 1 were obtained by a production method according to any one of the aforementioned Production Examples. The structures of these compounds were confirmed by an analyzer in the same manner as mentioned above.

Example 2

Measurement of Fluorescent Property of Compound

A 5 μM DMSO solution of each of the compounds shown in the following Table 1 was prepared. The excitation wavelength and fluorescence wavelength of the compound were measured by a FL4500 spectrofluorometric measuring machine manufactured by Hitachi High-Technologies Corporation.

TABLE 1

| Compound | Excitation wavelength λex | Fluorescence wavelength λem |
|---|---|---|
| Compound 1 | 485 | 575 |
| Compound 4 | 563 | 569 |
| Compound 5 | 560 | 628 |
| Compound 7 | 344 | 381 |
| Compound 10 | 586 | 615 |
| Compound 11 | 354 | 469 |
| Compound 14 | 491 | 510 |
| Compound 16 | 474 | 509 |
| Compound 17 | 492 | 511 |
| Compound 18 | 492 | 510 |
| Compound 20 | 516 | 602 |
| Compound 21 | 473 | 564 |
| Compound 22 | 553 | 570 |
| Compound 24 | 496 | 569 |
| Compound 26 | 684 | 710 |
| Compound 27 | 650 | 675 |
| Compound 28 | 589 | 614 |
| Compound 30 | 643 | 662 |
| Compound 34 | 638 | 661 |
| Compound 35 | 571 | 620 |
| Compound 37 | 650 | 770 |
| Compound 40 | 819 | 825 |
| Compound 43 | 797 | 816 |
| Compound 45 | 665 | 681 |
| Compound 46 | 679 | 715 |
| Compound 47 | 615 | 637 |
| Compound 49 | 830 | 831 |
| Compound 50 | 831 | 833 |
| Compound 54 | 774 | 800 |
| Compound 55 | 688 | 715 |
| Compound 59 | 804 | 520 |
| Compound 60 | 670 | 696 |

Example 3

Confirmation on Cancer Cell Inhibitory (Growth Suppressive) Action Against Pancreatic Cancer Cells

Experimental Example 1

Human pancreas cancer cells, KLM-1, were pre-cultured in RPMI1640 medium containing 10% FBS at 37° C. in a 5% $CO_2$ ambient. Thereafter, 4,000 cells were seeded per well of a 96-well plate and further cultured for 24 hours. Subsequently, Compound (1) was added to the medium so as to obtain a final concentration of 10 μg/mL and cultured at 37° C. for 24 hours in a 5% $CO_2$ ambient. The cultured cells were analyzed for viable cell count according to CellTiter-Glo Luminescent Cell Viability Assay (manufactured by Promega KK.). As a reference, the number of cells cultured in a medium containing a 0.1% dimethylsulfoxide solution (hereinafter, simply referred to as DMSO) in place of a medium containing Compound (1), in the aforementioned operation, was regarded as 100.

Experimental Examples 2 to 23

Viable cell count was analyzed in the same manner as in Experimental Example 1 except that Compound (1) of Experimental Example 1 was changed to another compounds shown in Table 2.

Comparative Examples 1 to 4

Viable cell count was analyzed in the same manner as in Experimental Example 1 except that Compound (1) was changed to comparative compounds 1 to 4.

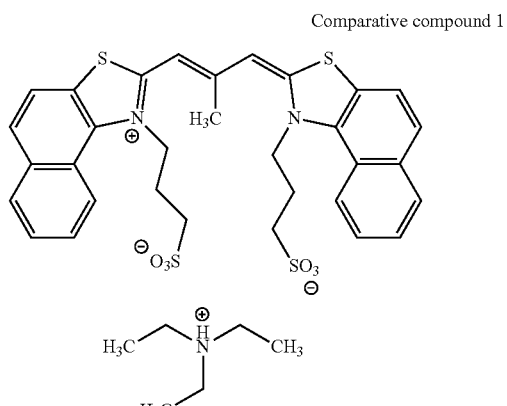

Comparative compound 1

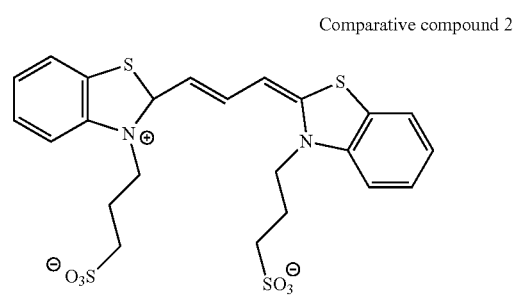

Comparative compound 2

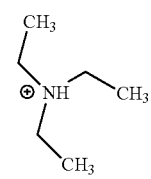

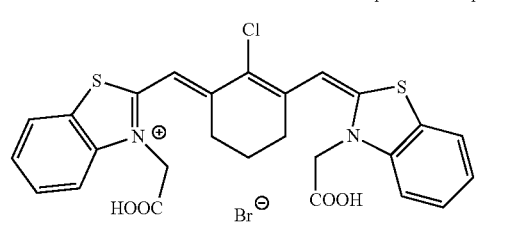

Comparative compound 3

-continued

Comparative compound 4

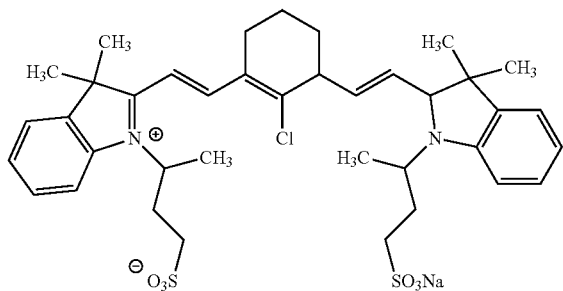

Viable cell counts of Experimental Examples 1 to 23 and Comparative Examples 1 to 4 were analyzed to obtain growth rates. The results are shown in Table 2. Evaluation of cancer cell inhibition against the pancreatic cancer cells (KLM-1) (growth suppression) was made based on the following criteria. Note that the growth rate used in Examples refers to the rate (expressed by percentage) of viable cell count after culture relative to the number of cells at the initiation of cell culture.

A: Cancer cell growth rate is less than 20% (cancer cell inhibitory (growth suppressive) effect is extremely high)

B: Cancer cell growth rate is 20% or more and less than 50% (cancer cell inhibitory (growth suppressive) effect is high)

C: Cancer cell growth rate is 50% or more (cancer cell inhibitory (growth suppressive) effect is low)

Table 2

TABLE 2

|  | Compound | Cancer cell growth rate (%) | Evaluation |
|---|---|---|---|
| Experimental Example 1 | Compound 1 | 31.9 | B |
| Experimental Example 2 | Compound 4 | 3.1 | A |
| Experimental Example 3 | Compound 5 | 6.4 | A |
| Experimental Example 4 | Compound 7 | 13.0 | A |
| Experimental Example 5 | Compound 10 | 13.5 | A |
| Experimental Example 6 | Compound 11 | 5.0 | A |
| Experimental Example 7 | Compound 16 | 2.0 | A |
| Experimental Example 8 | Compound 20 | 1.2 | A |
| Experimental Example 9 | Compound 21 | 38.2 | B |
| Experimental Example 10 | Compound 24 | 6.5 | A |
| Experimental Example 11 | Compound 26 | 8.6 | A |
| Experimental Example 12 | Compound 27 | 6.0 | A |
| Experimental Example 13 | Compound 30 | 18.8 | A |
| Experimental Example 14 | Compound 31 | 30.5 | B |
| Experimental Example 15 | Compound 34 | 26.6 | B |
| Experimental Example 16 | Compound 35 | 29.7 | B |
| Experimental Example 17 | Compound 37 | 4.8 | A |
| Experimental Example 18 | Compound 40 | 14.1 | A |
| Experimental Example 19 | Compound 43 | 35.6 | B |
| Experimental Example 20 | Compound 45 | 28.5 | B |
| Experimental Example 21 | Compound 46 | 16.7 | A |
| Experimental Example 22 | Compound 47 | 8.6 | A |
| Experimental Example 23 | Compound 49 | 12.0 | A |
| Comparative Example 1 | Comparative compound 1 | 87.0 | C |
| Comparative Example 2 | Comparative compound 2 | 86.0 | C |
| Comparative Example 3 | Comparative compound 3 | 93.0 | C |
| Comparative Example 4 | Comparative compound 4 | 75.0 | C |

As is apparent from Table 2, the compounds of the present invention have a high cancer cell inhibitory (growth suppressive) effect against the pancreatic cancer cells (KLM-1), compared to the comparative compounds.

Example 4

Observation on Cancer Cell Inhibitory (Growth Suppressive) Action Against Prostatic Cancer Cells Experimental Example 24

Prostatic cancer cells, PC-3, were pre-cultured in RPMI1640 medium containing 10% FBS at 37° C. in a 5% $CO_2$ ambient. Thereafter, 4,000 cells were seeded per well of a 96-well plate and further cultured for 24 hours. Subsequently, Compound (1) was added to the medium so as to obtain a final concentration of 10 μg/mL and cultured at 37° C. for 24 hours in a 5% $CO_2$ ambient. The cultured cells were analyzed for viable cell count according to Cell Titer-Glo Luminescent Cell Viability Assay (manufactured by Promega KK.). As a reference, the number of cells cultured in a medium containing a 0.1% dimethylsulfoxide solution (hereinafter, simply referred to as DMSO) in place of a medium containing Compound (1), in the aforementioned operation, was used as 100.

Experimental Examples 25 to 36

Viable cell count was analyzed in the same manner as in Experimental Example 24 except that Compound (1) of Experimental Example 24 was changed to each compound shown in Table 2.

Comparative Examples 5 to 8

Viable cell count was analyzed in the same manner as in Experimental Example 24 except that Compound (1) of Experimental Example 24 was changed to each of Comparative compounds 1 to 4, to obtain growth rates.

Note that the growth rate used in Examples refers to the rate (expressed by percentage) of viable cell count after culture relative to the number of cells at the initiation of cell culture. The results are shown in Table 3. Evaluation criteria are the same as in the above experiments. A cancer cell growth rate exceeding 100% indicates that cells are grown.

Cancer cell inhibition (growth suppression) against prostatic cancer cells (PC-3) was evaluated based on the following criteria.

A: Cancer cell growth rate is less than 20% (cancer cell inhibitory (growth suppressive) effect is extremely high)

B: Cancer cell growth rate is 20% or more and less than 50% (cancer cell inhibitory (growth suppressive) effect is high)

C: Cancer cell growth rate is 50% or more (cancer cell inhibitory (growth suppressive) effect is low)

Table 3

TABLE 3

|  | Compound | Cancer cell growth rate (%) | Evaluation |
|---|---|---|---|
| Experimental Example 24 | Compound 1 | 13.8 | A |
| Experimental Example 25 | Compound 4 | 19.5 | A |
| Experimental Example 26 | Compound 5 | 15.0 | A |
| Experimental Example 27 | Compound 7 | 15.3 | A |
| Experimental Example 28 | Compound 11 | 4.3 | A |
| Experimental Example 29 | Compound 16 | 8.4 | A |

TABLE 3-continued

| | Compound | Cancer cell growth rate (%) | Evaluation |
|---|---|---|---|
| Experimental Example 30 | Compound 20 | 13.1 | A |
| Experimental Example 31 | Compound 24 | 10.0 | A |
| Experimental Example 32 | Compound 27 | 7.7 | A |
| Experimental Example 33 | Compound 43 | 12.3 | A |
| Experimental Example 34 | Compound 46 | 17.7 | A |
| Experimental Example 35 | Compound 47 | 13.8 | A |
| Experimental Example 36 | Compound 49 | 5.3 | A |
| Comparative Example 5 | Comparative compound 1 | 105 | C |
| Comparative Example 6 | Comparative compound 2 | 68.0 | C |
| Comparative Example 7 | Comparative compound 3 | 101 | C |
| Comparative Example 8 | Comparative compound 4 | 88.3 | C |

As is apparent from Table 3, the compounds of the present invention have a high cancer cell inhibitory (growth suppressive) effect against the prostatic cancer cells (PC-3), compared to comparative compounds.

Example 5

Observation on Cancer Stem-Cell Selective Inhibitory Action Against Chronic Myelocytic Leukemia Cells Experimental Examples 37

Human chronic myelocytic leukemia cells, K562, were pre-cultured in RPMI1640 medium containing 10% FBS at 37° C. in a 5% $CO_2$ ambient. Then, a fraction containing 80% or more of cancer stem cells was extracted by use of a cancer stem cell marker, ALDEFLUOR reagent (manufactured by VERITAS Corporation) and FACSAria flow cytometry (manufactured by Nippon Becton, Dickinson and Company). Subsequently, Compound (16) was added to the medium so as to obtain a final concentration of 0.05 µg/mL and cultured at 37° C. for 24 hours in a 5% $CO_2$ ambient. The cultured cells were analyzed for viable cell count according to CellTiter-Glo Luminescent Cell Viability Assay (manufactured by Promega KK.). As a reference, the number of cells cultured in a medium containing a 0.1% dimethylsulfoxide solution (hereinafter, simply referred to as DMSO) in place of a medium containing Compound (1), in the aforementioned operation, was used as 0.1. Note that hereinafter, an ALDEFLUOR reagent positive fraction (deemed as cancer stem cells) is represented by ALDH (+), whereas an ALDEFLUOR reagent negative fraction (not deemed as cancer stem cells) is represented by ALDH (−), in some cases.

Experimental Examples 38 to 70

The same operation as in Experimental Example 37 was repeated except that Compound (16) in Experimental Example 37 was changed to the other compounds and final concentrations shown in Table 3 were used and viable cell counts were separately analyzed.

Comparative Examples 9 to 16

The same operation as in Experimental Example 37 was repeated except that Compound (16) in Experimental Example 37 was changed to Imatinib (manufactured by NOVARTIS), which is a general anticancer drug, and comparative compounds shown in Table 3 and final concentrations shown in Table 3 were used and viable cell counts were separately analyzed.

The results of Experimental Examples 37 to 70 and Comparative Examples 9 to 16 are collectively shown in Table 4. Further, the growth suppressive effect of cancer stem cells was evaluated based on the following criteria. Note that the growth rate in Examples is a value obtained by dividing viable cell count after culture by the number of cells at the initiation time of culture.

A: The growth rate of ALDH (+) is less than 0.5 (growth suppressive effect against cancer stem cells is extremely high)

B: The growth rate of ALDH (+) is 0.5 or more and less than 0.95

(growth suppressive effect against cancer stem cells is high)

C: The growth rate of ALDH (+) is 0.95 or more (no growth suppressive effect against cancer stem cells)

Furthermore, superiority evaluation of cancer stem cells was evaluated by comparing cancer stem cells to cancer cells based on the following criteria.

A: The value of the growth rate of ALDH (+)/the growth rate of ALDH (−) is less than 0.8 (selective inhibitory effect against cancer stem cells is extremely high)

B: The value of the growth rate of ALDH (+)/the growth rate of ALDH (−) is 0.8 or more and less than 0.95 (selective inhibitory effect against cancer stem cells is high)

C: The value of the growth rate of ALDH (+)/the growth rate of ALDH (−) is 0.95 or more (no selective inhibitory effect against cancer stem cells)

TABLE 4

| | Compound | Amount of dye | ALDH(+) | Growth suppression evaluated | ALDH(−) | ALDH(+)/ALDH(−) | ALDH(+) Superiority evaluation |
|---|---|---|---|---|---|---|---|
| Experimental Example 37 | 35 | 0.05 µg/ml | 0.67 | B | 0.87 | 0.77 | A |
| Experimental Example 38 | 35 | 0.5 µg/ml | 0.43 | A | 0.66 | 0.66 | A |
| Experimental Example 39 | 35 | 1 µg/ml | 0.44 | A | 0.49 | 0.90 | B |
| Experimental Example 40 | 16 | 0.05 µg/ml | 0.68 | B | 0.78 | 0.87 | B |
| Experimental Example 41 | 16 | 0.5 µg/ml | 0.36 | A | 0.52 | 0.70 | A |
| Experimental Example 42 | 16 | 1 µg/ml | 0.16 | A | 0.34 | 0.47 | A |
| Experimental Example 43 | 24 | 0.05 µg/ml | 0.61 | B | 0.75 | 0.81 | B |
| Experimental Example 44 | 24 | 0.5 µg/ml | 0.39 | A | 0.63 | 0.61 | A |
| Experimental Example 45 | 24 | 1 µg/ml | 0.19 | A | 0.39 | 0.48 | A |
| Experimental Example 46 | 27 | 10 µg/ml | 0.07 | A | 0.13 | 0.56 | A |
| Experimental Example 47 | 32 | 10 µg/ml | 0.09 | A | 0.29 | 0.32 | A |
| Experimental Example 48 | 21 | 10 µg/ml | 0.27 | A | 0.41 | 0.66 | A |

TABLE 4-continued

|  | Compound | Amount of dye | ALDH(+) | Growth suppression evaluated | ALDH(−) | ALDH(+)/ALDH(−) | ALDH(+) Superiority evaluation |
|---|---|---|---|---|---|---|---|
| Experimental Example 49 | 1 | 10 μg/ml | 0.45 | A | 0.52 | 0.87 | B |
| Experimental Example 50 | 34 | 10 μg/ml | 0.48 | A | 0.67 | 0.72 | A |
| Experimental Example 51 | 35 | 10 μg/ml | 0.55 | B | 0.80 | 0.69 | A |
| Experimental Example 52 | 5 | 10 μg/ml | 0.71 | B | 0.90 | 0.79 | A |
| Experimental Example 53 | 33 | 10 μg/ml | 0.83 | B | 1.00 | 0.84 | B |
| Experimental Example 54 | 56 | 10 μg/ml | 0.42 | A | 0.65 | 0.65 | A |
| Experimental Example 55 | 57 | 10 μg/ml | 0.55 | B | 0.68 | 0.81 | B |
| Experimental Example 56 | 58 | 10 μg/ml | 0.70 | B | 0.85 | 0.82 | B |
| Experimental Example 57 | 14 | 10 μg/ml | 0.38 | A | 0.49 | 0.77 | A |
| Experimental Example 58 | 17 | 10 μg/ml | 0.04 | A | 0.13 | 0.30 | A |
| Experimental Example 59 | 17 | 1 μg/ml | 0.69 | B | 0.79 | 0.87 | B |
| Experimental Example 60 | 18 | 10 μg/ml | 0.04 | A | 0.13 | 0.29 | A |
| Experimental Example 61 | 22 | 10 μg/ml | 0.22 | A | 0.29 | 0.75 | A |
| Experimental Example 62 | 28 | 10 μg/ml | 0.30 | A | 0.43 | 0.69 | A |
| Experimental Example 63 | 28 | 1 μg/ml | 0.65 | B | 0.77 | 0.83 | B |
| Experimental Example 64 | 54 | 10 μg/ml | 0.07 | A | 0.13 | 0.50 | A |
| Experimental Example 65 | 55 | 10 μg/ml | 0.04 | A | 0.11 | 0.33 | A |
| Experimental Example 66 | 59 | 10 μg/ml | 0.02 | A | 0.10 | 0.22 | A |
| Experimental Example 67 | 59 | 1 μg/ml | 0.14 | A | 0.21 | 0.67 | A |
| Experimental Example 68 | 60 | 10 μg/ml | 0.04 | A | 0.12 | 0.34 | A |
| Experimental Example 69 | 50 | 10 μg/ml | 0.05 | A | 0.12 | 0.42 | A |
| Experimental Example 70 | 51 | 10 μg/ml | 0.03 | A | 0.11 | 0.27 | A |
| Comparative Example 9 | Imatinib | 0.12 μg/ml | 0.74 | B | 0.51 | 1.47 | C |
| Comparative Example 10 | Imatinib | 0.24 μg/ml | 0.59 | B | 0.40 | 1.48 | C |
| Comparative Example 11 | Imatinib | 0.35 μg/ml | 0.48 | A | 0.32 | 1.51 | C |
| Comparative Example 12 | Imatinib | 0.47 μg/ml | 0.36 | A | 0.22 | 1.63 | C |
| Comparative Example 13 | Imatinib | 0.59 μg/ml | 0.31 | A | 0.11 | 2.80 | C |
| Comparative Example 14 | Comparative compound 1 | 1 μg/ml | 1.00 | C | 0.94 | 1.06 | C |
| Comparative Example 15 | Comparative compound 2 | 1 μg/ml | 0.99 | C | 1.21 | 0.82 | C |
| Comparative Example 16 | Comparative compound 3 | 1 μg/ml | 1.09 | C | 1.38 | 0.79 | C |

Note that, in the cases of Comparative Examples 14 to 16, ALDH (+) is close to almost 1. This indicates that no suppressive effect is obtained. In contrast, a numerical value of 1 or more as an ALDH (−) value indicates that the number of cancer cells increases.

As is apparent from Table 4, it is confirmed that the compounds of the present invention has a selective inhibitory effect against cancer stem cells. More specifically, when a general anticancer agent, Imatinib, was used, an inhibitory effect against general cancer cells was observed; however, no inhibitory effect was confirmed when comparative compounds were used.

Example 6

Confirmation of Cancer Stem-Cell Selective Staining to Chronic Myelocytic Leukemia Cells Experimental Examples 71 to 73

The cells cultured for 24 hours in each of Experimental Examples 39, 42 and 45 were subjected to nuclear staining with Hoechest33342 (manufactured by Dojindo Laboratories) and a fluorescent image observed under AXIOVERT200M inverted fluorescent microscope (manufactured by Carl Zeiss) was photographed. The ratio of ALDH (+) cells stained and the ratio (percentage) of ALDH (−) cells stained in each compound are shown in Table 5.

TABLE 5

|  | Compound | ALDH(+) | ALDH(−) | Selective staining of cancer stem cells |
|---|---|---|---|---|
| Example 71 | 35 | 82.5 | 21.4 | ALDH (+) cells are selectively stained |
| Example 72 | 16 | 99.5 | 18.6 | ALDH (+) cells are selectively stained |
| Example 73 | 24 | 81.2 | 28.6 | ALDH (+) cells are selectively stained |

As is apparent from Table 5, it is found that the compound of the present invention selectively stains cancer stem cells (ALDH (+)) than general cancer cells (ALDH (−)).

Example 7

Confirmation of Inhibitory Action in Cancer Stem Cells Transplanted Animal

Experimental Example 74

From cell strain K562-KOr, which is a strain of human chronic myelocytic leukemia cells having fluorescent protein Kusabira-Orange constantly expressed, a fraction (ALDH (+)) containing 80% or more of cancer stem cells was extracted by use of a cancer stem cell marker, ALDEFLUOR reagent (manufactured by VERITAS Corporation) and FACSAria flow cytometry (manufactured by Nippon Becton, Dickinson and Company). The ALDH (+) fraction and a ALDH (−) fraction of general cancer cells were transplanted separately to zebra young fish (MieKomachi lineage, 2 days after fertilization) and the fish were raised in a 32° C. environment. Furthermore, 24 hours after transplantation, Compound (16) was added to breeding water so as to obtain a final concentration of 0.5 μm and fish were raised for two days in a 32° C. environment.

Cells transplanted to the zebra young fish were observed under MZ16F fluorescent stereoscopic microscope (manufactured by Leica Microsystems) and a fluorescent image of the cells after 24 hours was photographed and then fluorescent intensity was quantified.

As a reference, the fluorescent intensity of cells, which were cultured in the same operation method as above in a medium containing a 0.1% DMSO solution in place of Compound (16), was used.

Comparative Example 17

The numerical value of fluorescent intensity was obtained from a fluorescent image taken in the same manner as in Experimental Example 74 except that Compound (16) of Experimental Example 74 was changed to Imatinib.

The inhibition rates of ALDH (+)/ALDH (−) cell transplanted to zebra young fish in Experimental Example 74 and Comparative Example 17 are shown in Table 6. The inhibition rate herein was obtained according to the expression: $100 \times (1 - F1/F0)$, where the fluorescent intensity of cells when a test substance was added is represented by F1, and the fluorescent intensity of cells when a reference substance (DMSO) was added is represented by F0.

TABLE 6

| | Compound | ALDH(+) | ALDH(−) | Growth suppression rate |
|---|---|---|---|---|
| Example 74 | 16 | 95.0 | 82.0 | ALDH(+) is high |
| Comparative Example 17 | Imatinib | 60.0 | 80.0 | ALDH(−) is high |

As is apparent form Table 6, it was confirmed that the size of tumor (fluorescent region) is small compared to the case where neither compound nor Imatinib was administered. Particularly, in the group in which the compound of the present invention is administered, it was confirmed that an effect of suppressing a tumor size is preferentially obtained in a cancer stem cell (ALDH (+)) transplanted model animal.

Example 8

Confirmation of Cancer Metastasis Suppressive Effect in Cancer Cell Metastatic Foci (Region within 300 to 450 μm from a Transplanted Tumor)

Experimental Example 75

From cell strain K562-KOr, in which KLM1 cells have fluorescent protein Kusabira-Orange constantly expressed, a fraction (ALDH (+)) containing 80% or more of cancer stem cells was extracted with ALDEFLUOR reagent (manufactured by VERITAS Corporation) and FACSAria flow cytometry (manufactured by Nippon Becton, Dickinson and Company). The extracted KLM1-KOr cells were transplanted to zebra young fish (MieKomachi lineage, 2 days after fertilization) and the fish were raised in a 32° C. environment. Furthermore, 24 hours after transplantation, Compound (26) (745 μmol/KgBW) was administered to yolk sac.

72 hours later, cells transplanted to the zebra young fish were observed under MZ16F fluorescent stereoscopic microscope (manufactured by Leica Microsystems) and a fluorescent image of the region within 300 to 450 μm from a transplanted tumor was photographed and then fluorescent intensity was quantified.

As a reference, the fluorescent intensity of cells, which were cultured in the same operation method as above in a medium containing a 0.1% DMSO solution in place of Compound (26), was used.

Comparative Examples 18 and 19

Fluorescent images were photographed in the same manner as in Experimental Example 26 except that Imatinib and Dasatinib were respectively used in place of the compound (26) in Experimental Example 75.

The cancer cell inhibition rates of metastatic foci of cancer cells (in the region within 300 to 450 μm from a transplanted tumor) transplanted to zebra young fish in Experimental Example 75 and Comparative Examples 18 and 19 are shown in Table 6.

The inhibition rate herein was obtained according to the expression: $100 \times (1 - F1/F0)$, where the fluorescent intensity of cells when a test substance was added is represented by F1, and the fluorescent intensity of cells when a reference substance (DMSO) was added is represented by F0.

The growth suppressive effect in metastatic foci (region within 300 to 450 μm from a transplanted tumor) of cancer stem cells was evaluated based on the following criteria.

A: Inhibition rate is 70 or more (growth suppressive effect against metastatic foci (region within 300 to 450 μm from a transplanted tumor) of cancer stem cells is extremely high)

B: Inhibition rate is 50 or more and less than 70

(growth suppressive effect against metastatic foci (region within 300 to 450 μm from a transplanted tumor) of cancer stem cells is high)

C: Inhibition rate is less than 50

(growth suppressive effect against metastatic foci (region within 300 to 450 μm from a transplanted tumor) of cancer stem cells is low)

TABLE 7

| | Compound | Inhibition rate | Evaluation |
|---|---|---|---|
| Example 75 | 26 | 80 | A |
| Comparative Example 18 | Imatinib | 60 | B |
| Comparative Example 19 | Dasatinib | 36 | C |

As is apparent from Table 7, it was confirmed that the cancer stem-cell inhibition drug of the present invention has a higher metastasis suppressive effect than known anticancer agents used as comparison.

INDUSTRIAL APPLICABILITY

The compound provided by the present invention is useful as a cancer cell inhibitory drug. Furthermore, owing to the cancer cell inhibitory drug provided by the present invention, growth suppression, cellular division suppression, metastasis suppression, functional inhibition and cytocidal action of cancer cells, particularly cancer stem cells, can be mediated. In addition, cancer stem cells can be easily detected and the site of cancer stem cells can be accurately specified. The compound of the present invention is expected to widely contribute to the medical industry.

The invention claimed is:
1. A method of inhibiting growth of any one of a pancreatic cancer cell, a prostatic cancer cell, and a cancer stem cell of chronic myelocytic leukemia in a subject in need thereof, comprising administering to the subject a composition comprising, as an active ingredient, any one of compounds (2) to (13) and (15) to (60).
(2)
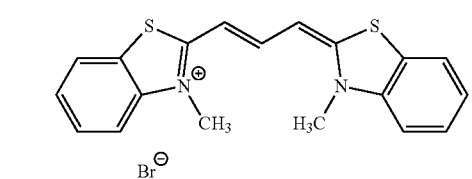
(3)
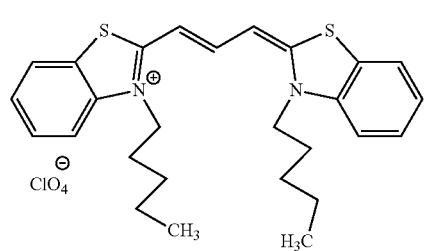
(4)
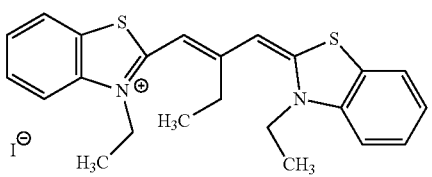
(5)
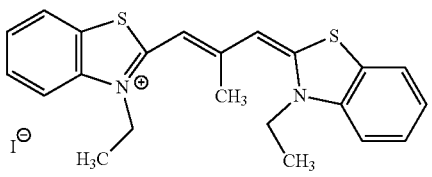
(6)
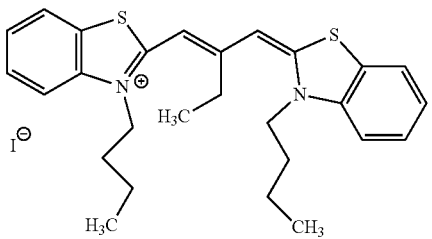
(7)
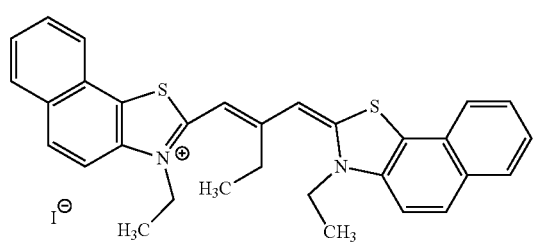
(8)
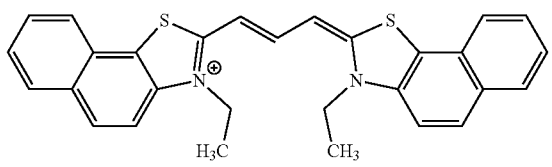
(9)
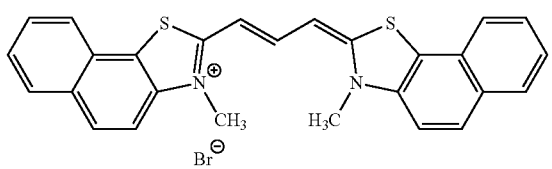
(10)
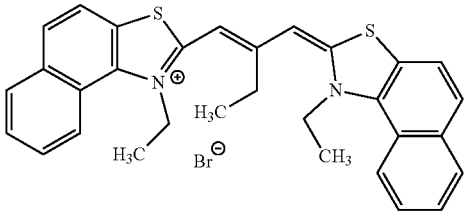
(11)
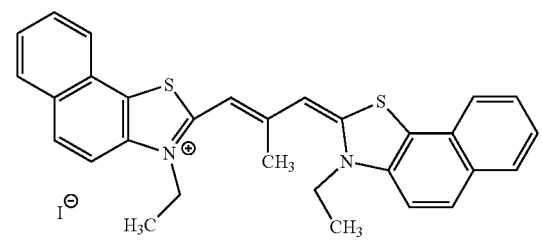
(12)
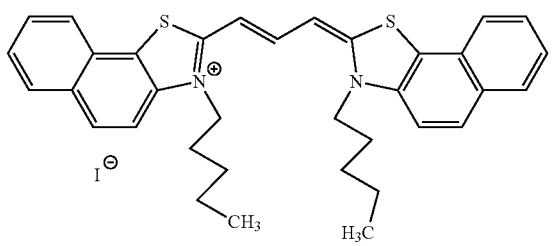
(13)
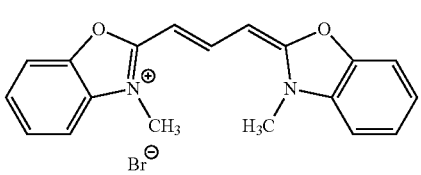
(15)
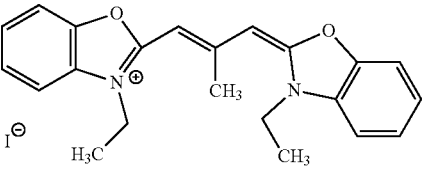

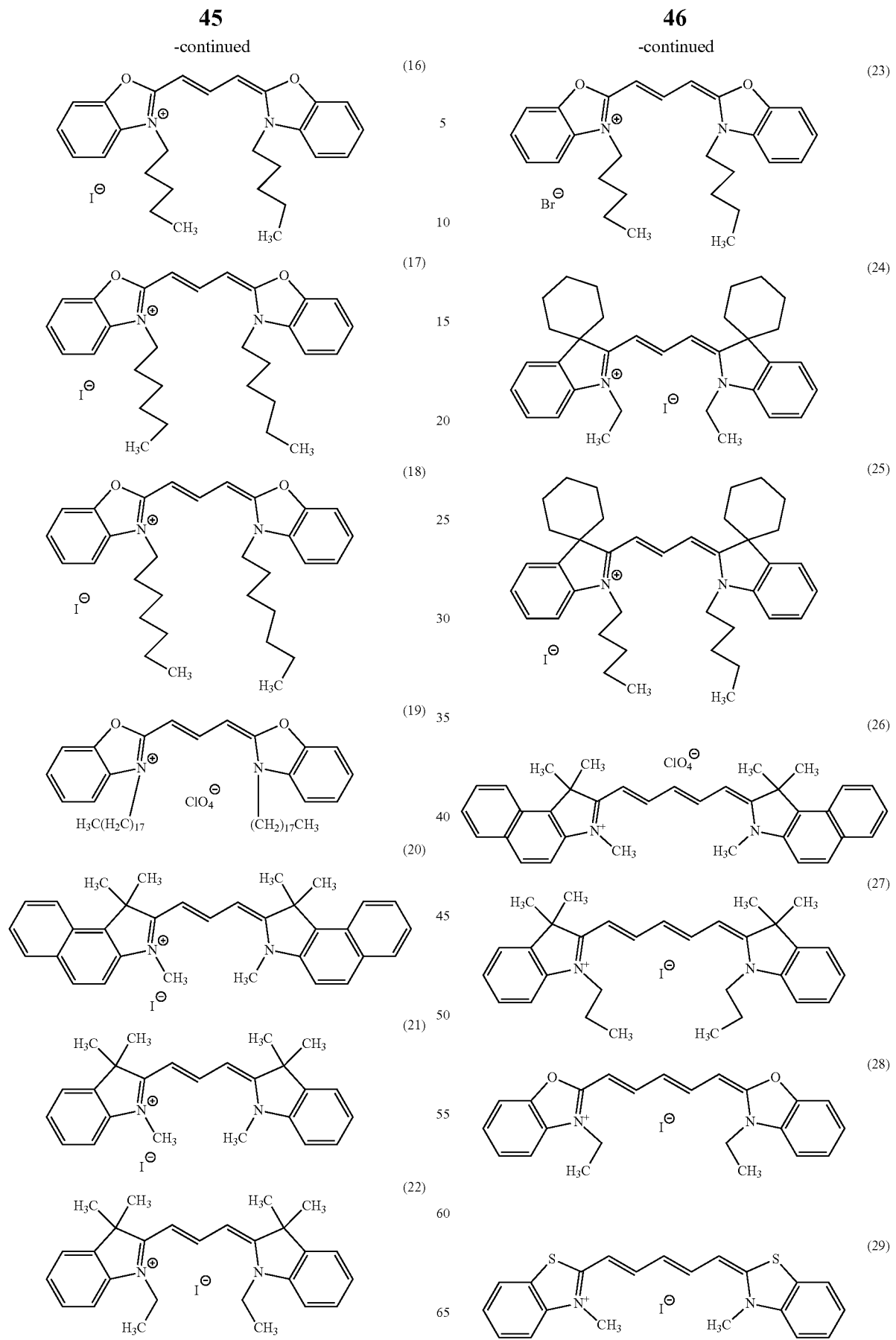

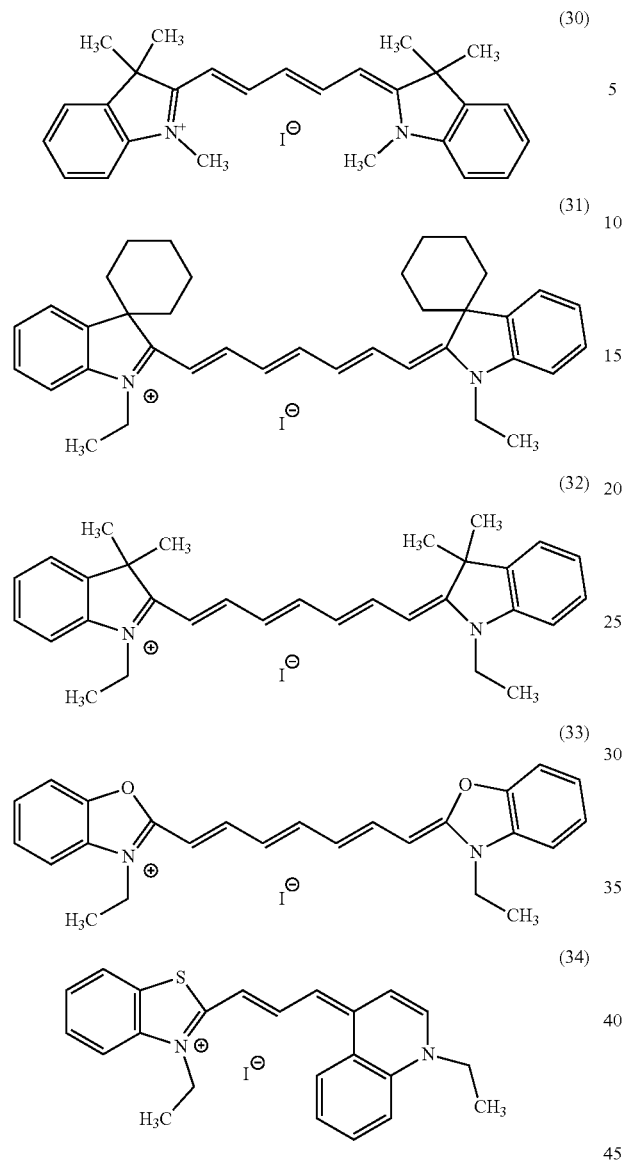
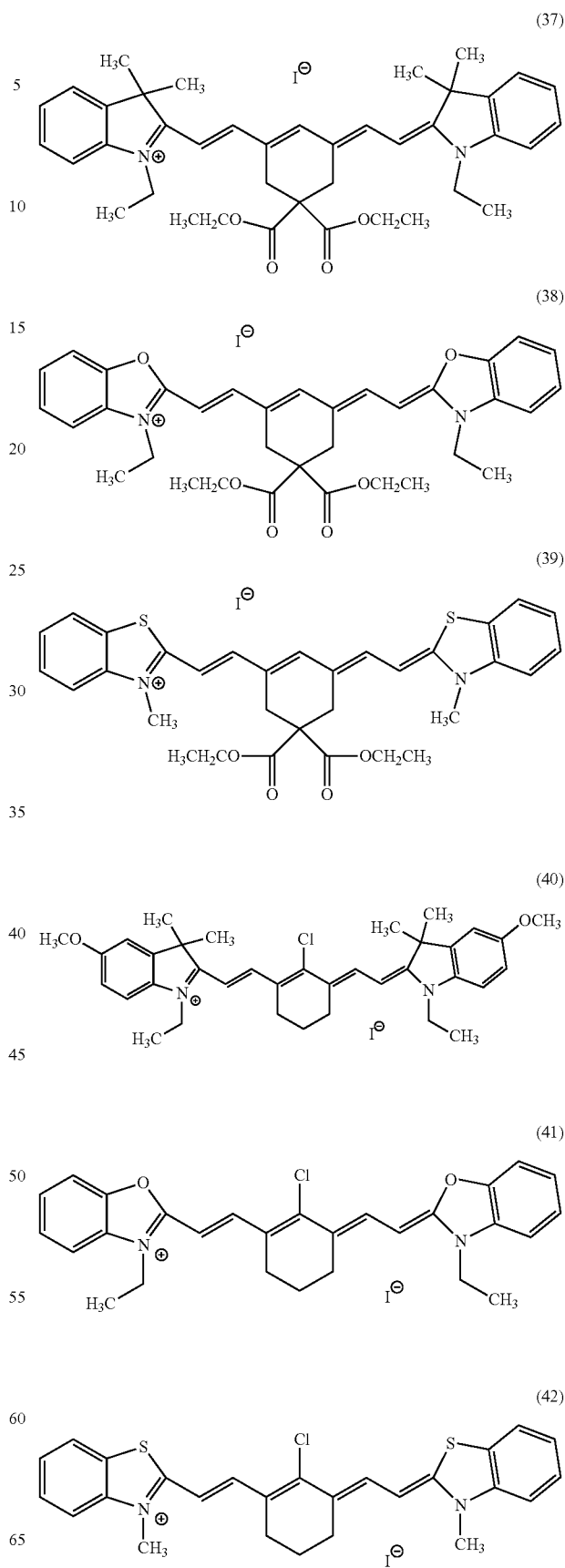

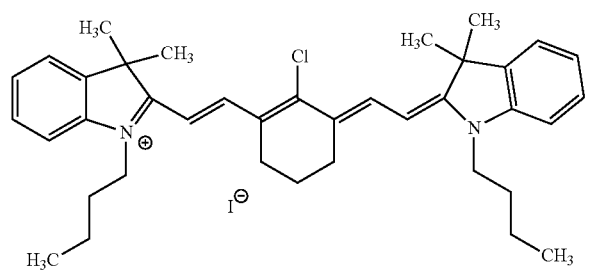
(43)
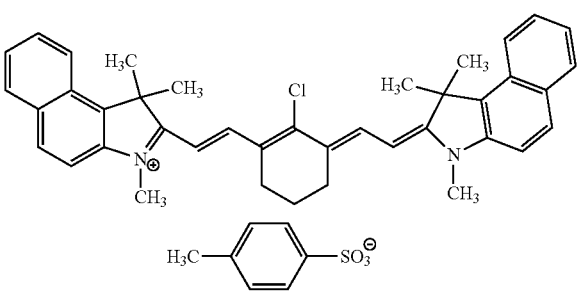
(49)
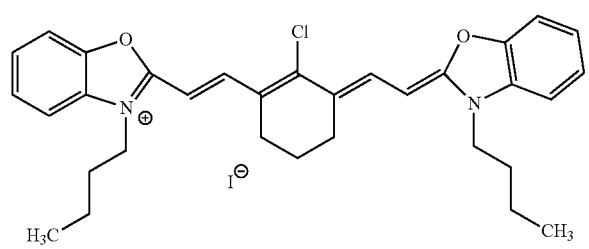
(44)
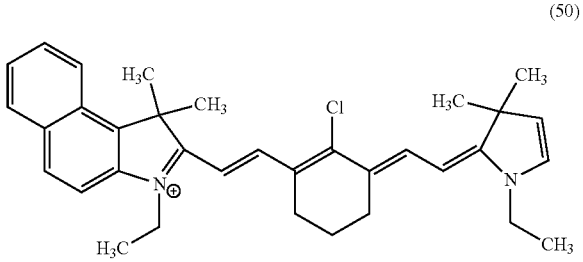
(50)
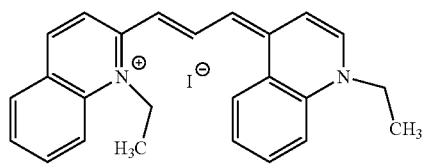
(45)
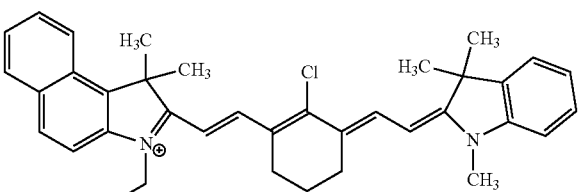
(51)
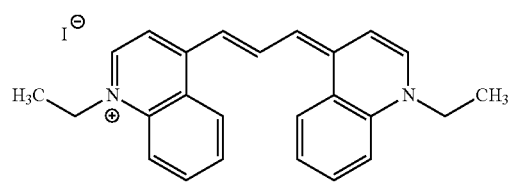
(46)
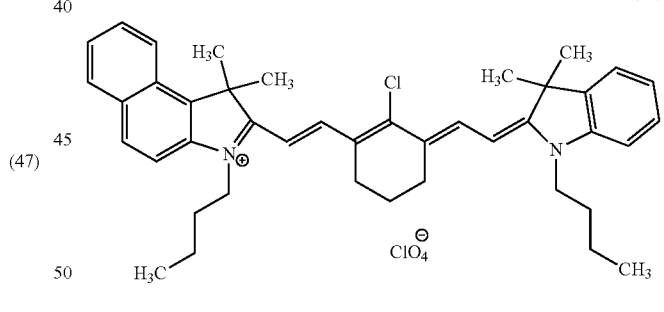
(52)
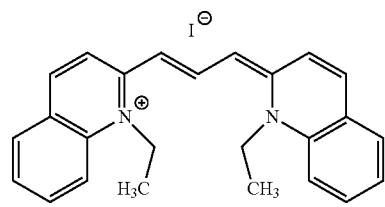
(47)
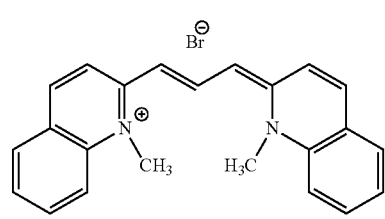
(48)
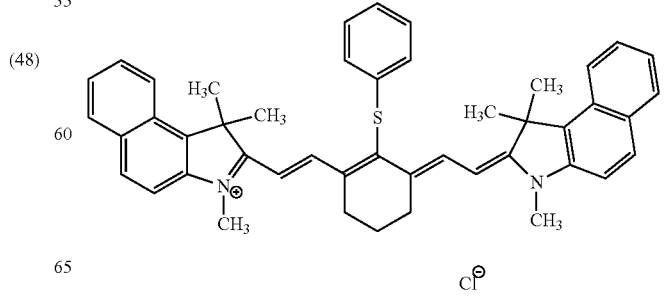
(53)

(54)
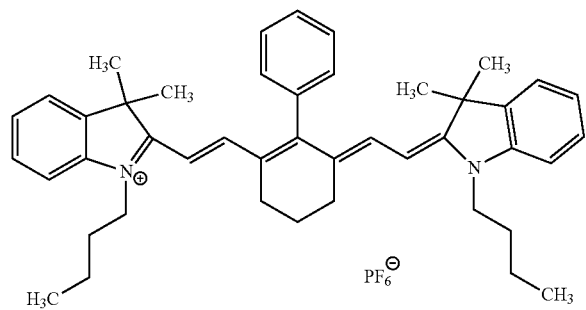

(55)
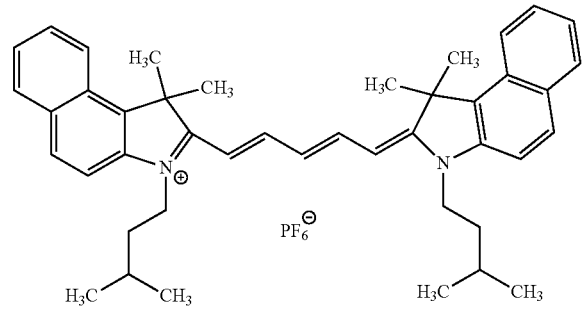

(56)
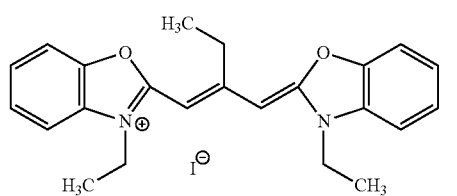

(57)
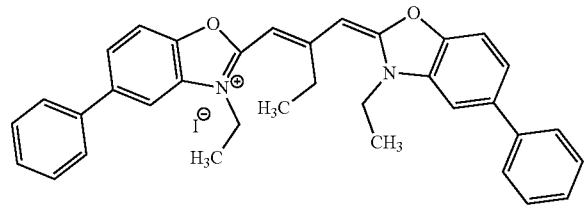

(58)
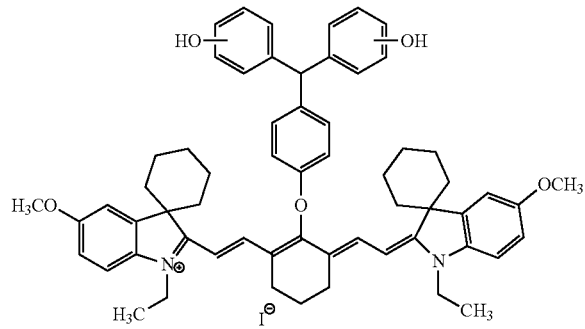

(59)
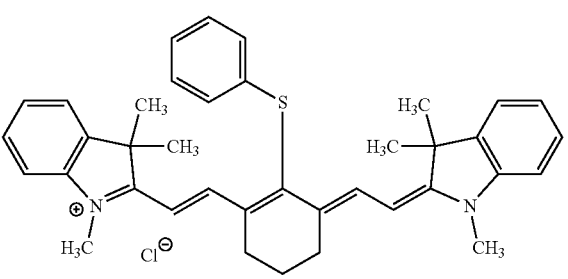

(60)
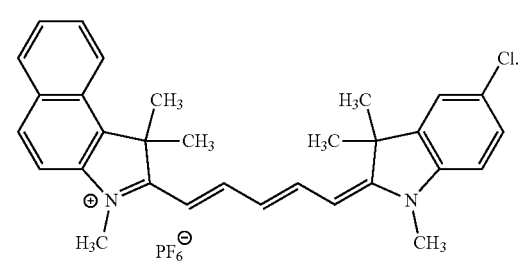

2. The method according to claim 1, wherein the subject is a human.

3. A method of detecting a composition taken into a cancer cell selected from the group consisting of a pancreatic cancer cell, a prostatic cancer cell, and a cancer stem cell of chronic myelocytic leukemia in a subject in need thereof, comprising:

administering to the subject a composition comprising, as an active ingredient, a compound selected from the group consisting of compounds (2) to (13) and (15) to (60); and detecting the composition taken into the cancer cell:

(2)
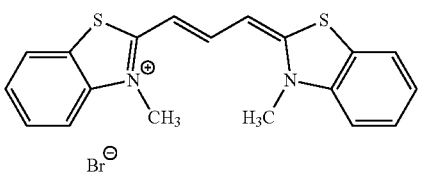

(3)
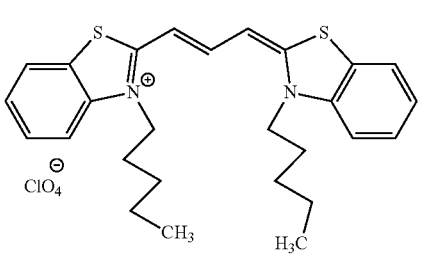

(4)
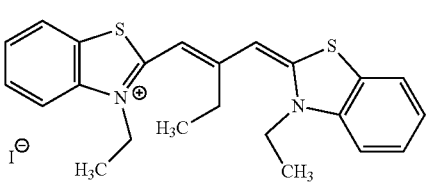

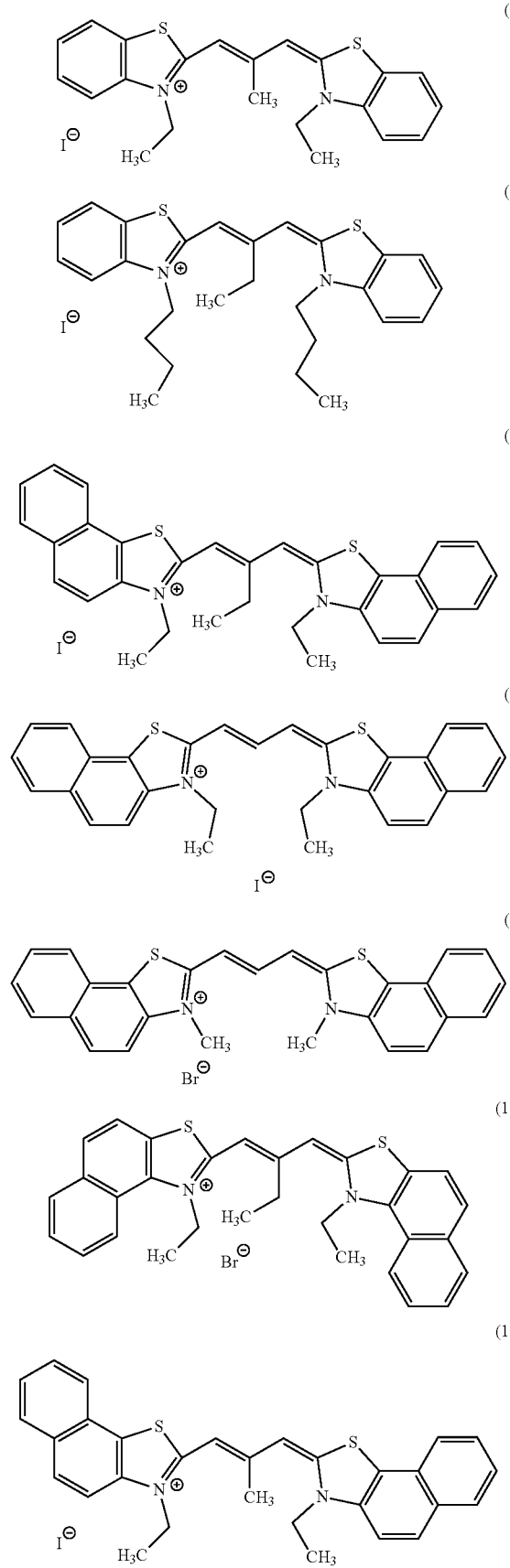
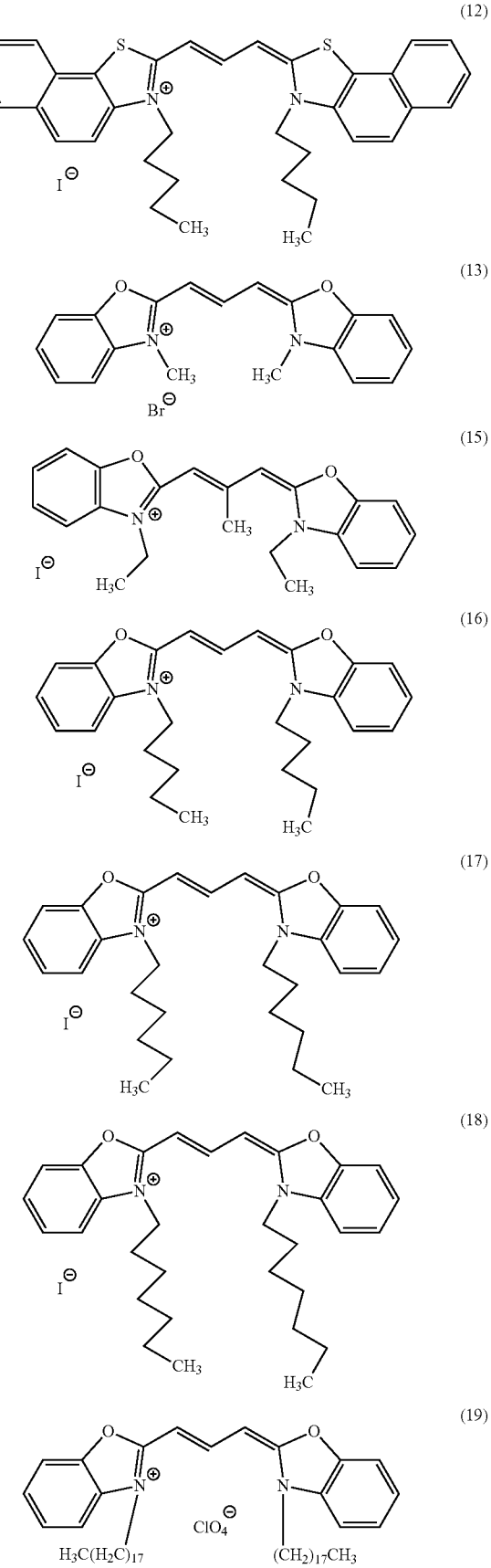

-continued
(20)
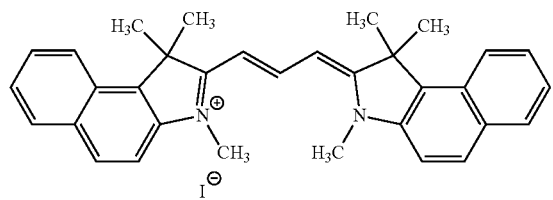
(21)
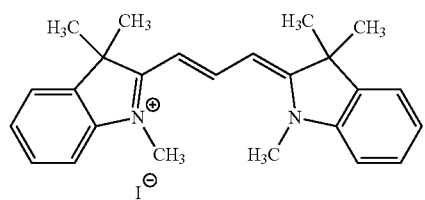
(22)
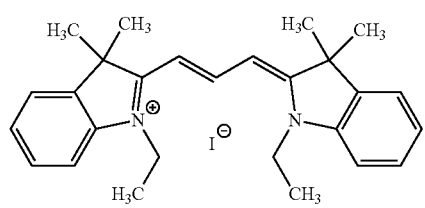
(23)
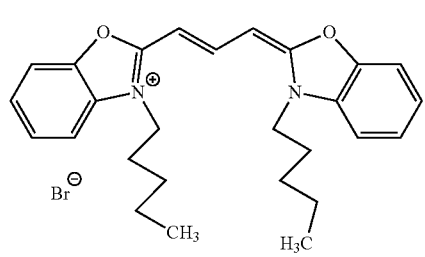
(24)
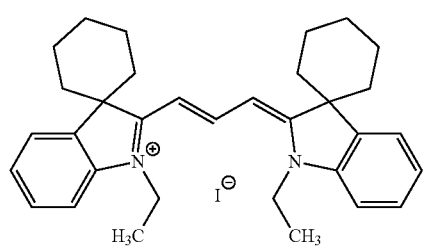
(25)
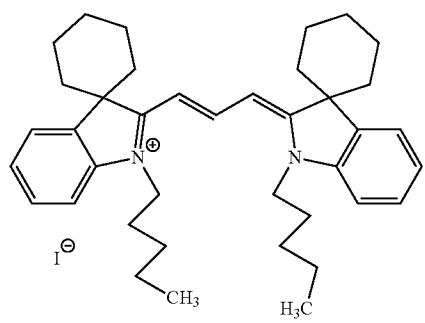
(26)
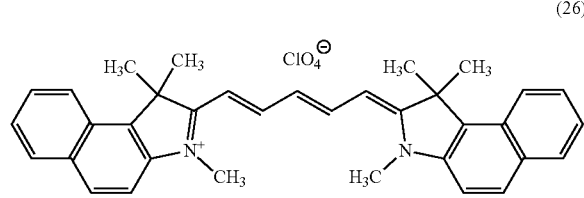
-continued
(27)
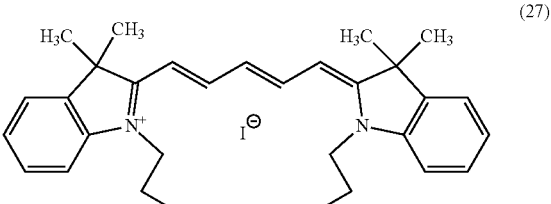
(28)
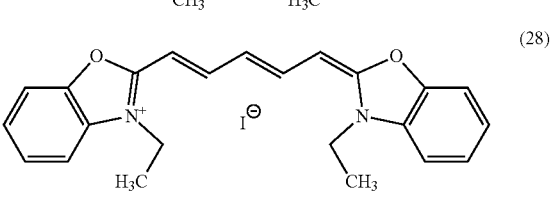
(29)
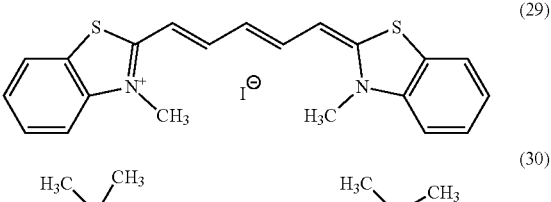
(30)
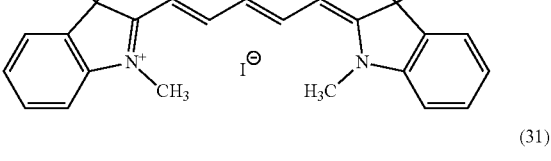
(31)
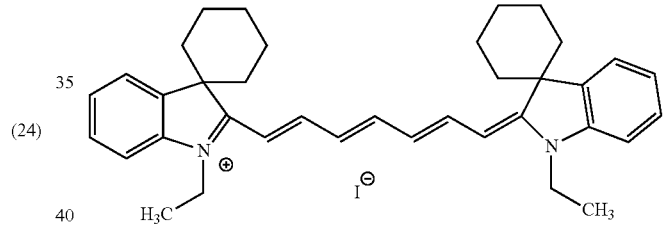
(32)
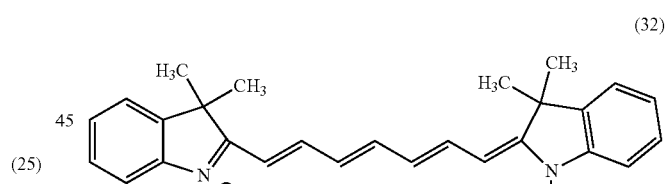
(33)
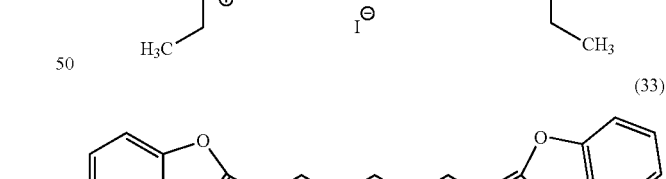
(34)
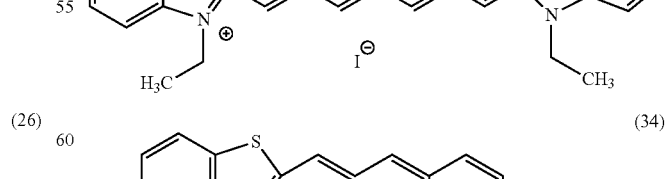

-continued
(35)
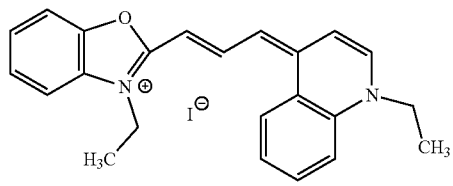
(36)
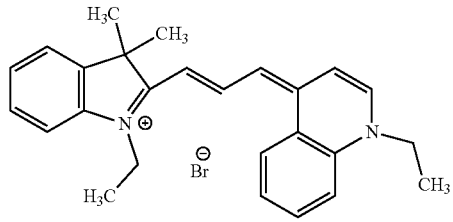
(37)
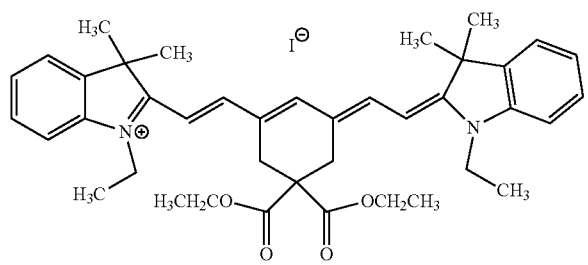
(38)
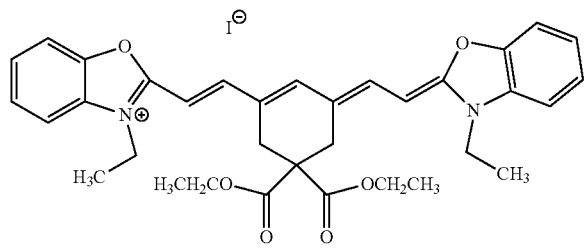
(39)
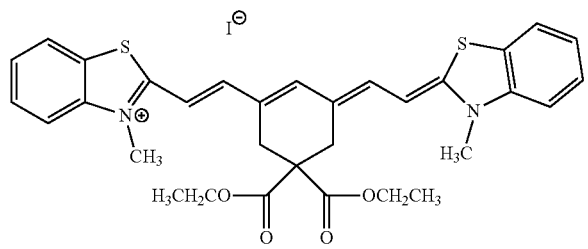
(40)
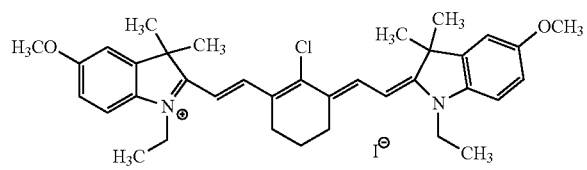
(41)
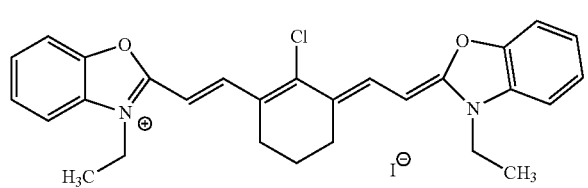
-continued
(42)
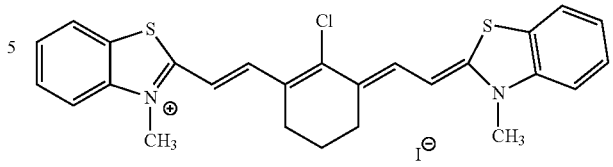
(43)
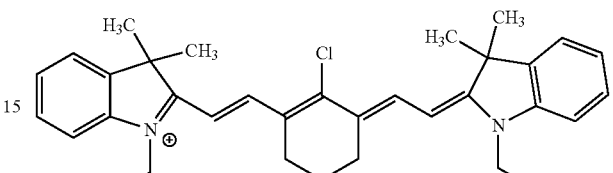
(44)
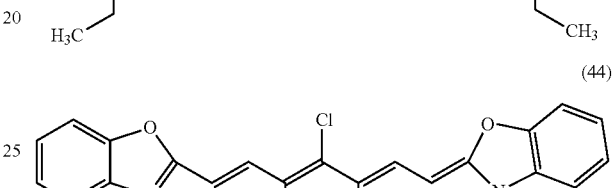
(45)
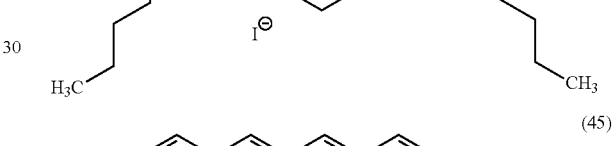
(46)
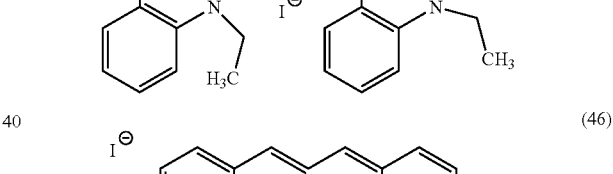
(47)
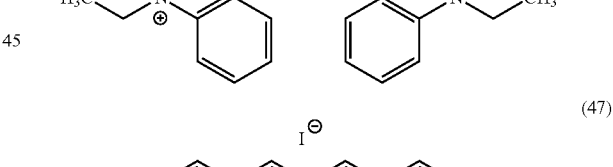
(48)
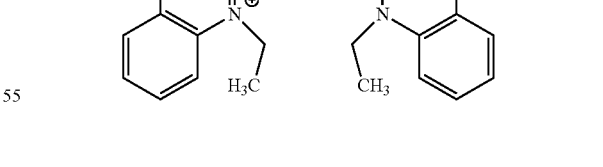

(49)
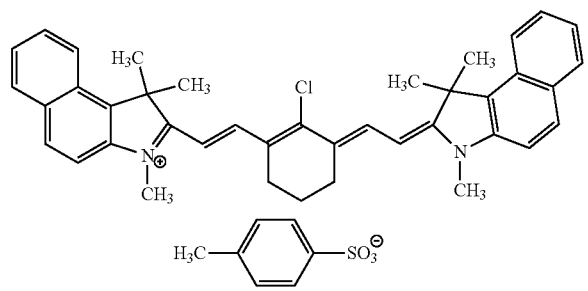
(50)
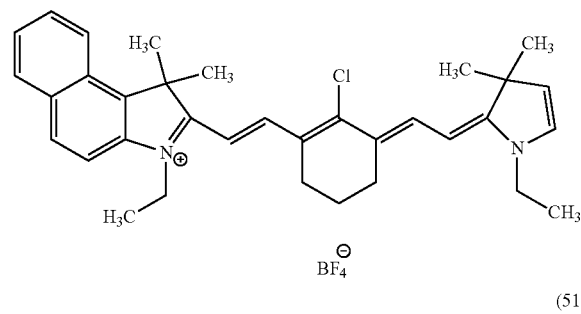
(51)
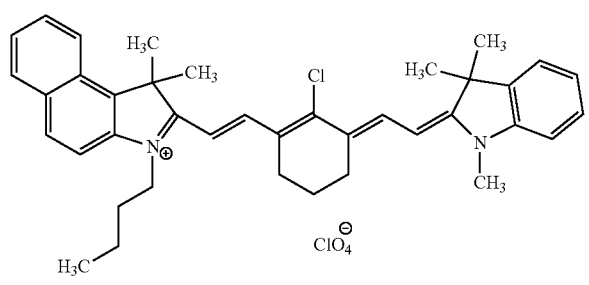
(52)
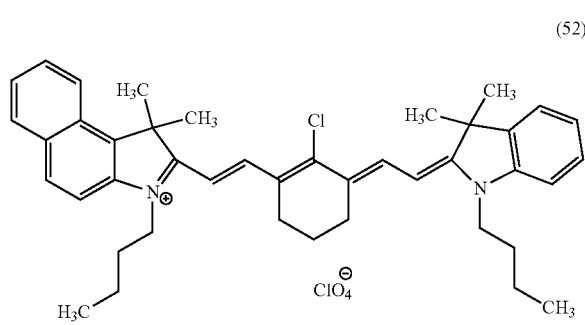
(53)
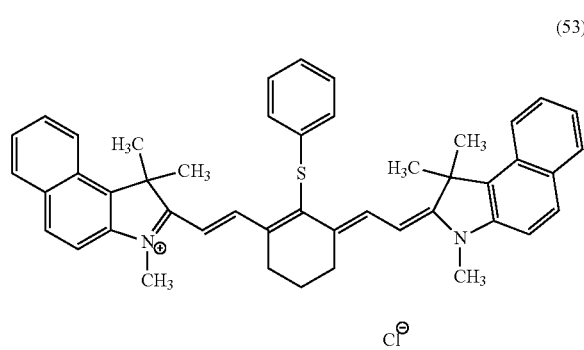
(54)
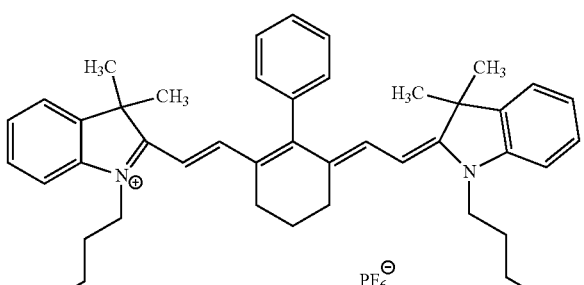
(55)
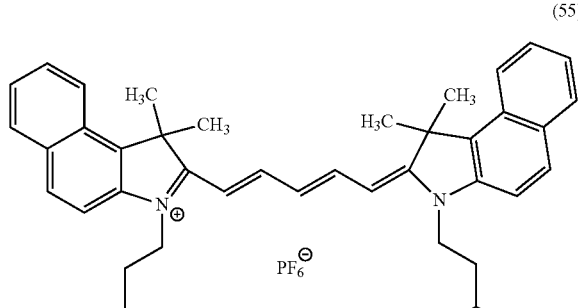
(56)
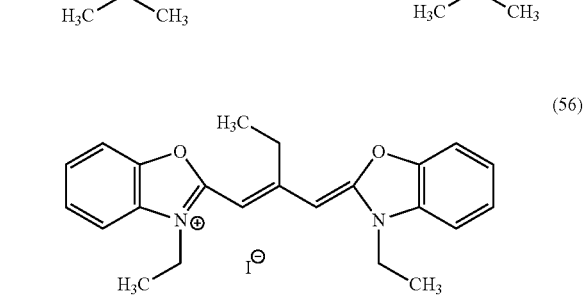
(57)
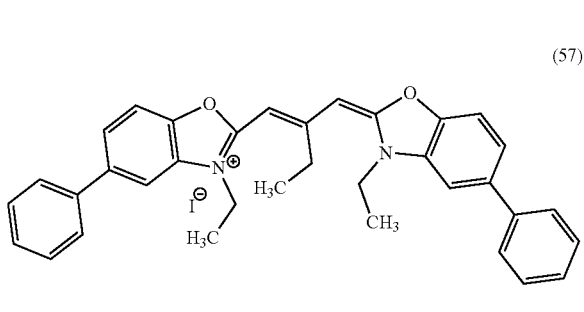
(58)
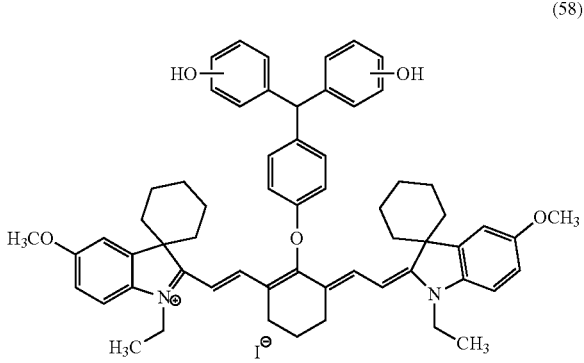

(59)
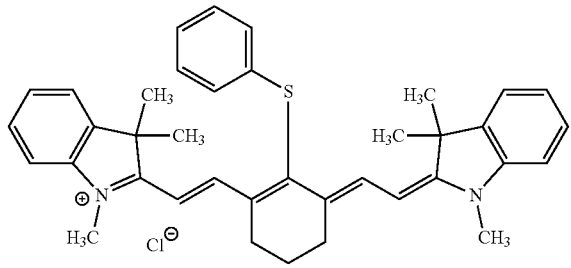

(60)
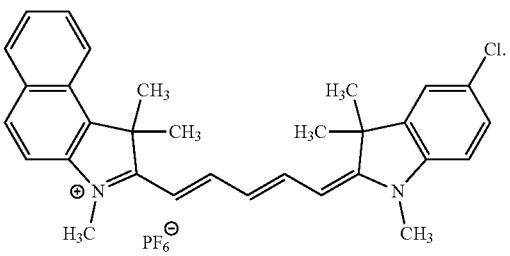

4. A method of screening a cancer cell selected from the group consisting of a pancreatic cancer cell, a prostatic cancer cell, and a cancer stem cell of chronic myelocytic leukemia in a subject in need thereof, comprising:
  administering to the subject a composition comprising, as an active ingredient, any one of compounds (2) to (13) and (15) to (60); and
  detecting the cancer cell selectively:

(2)
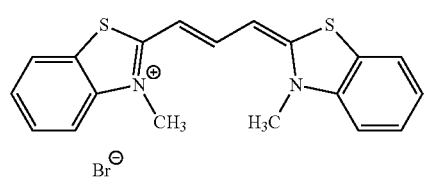

(3)
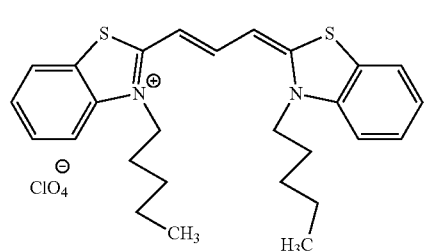

(4)
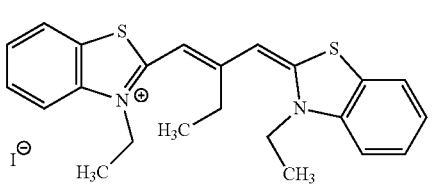

(5)
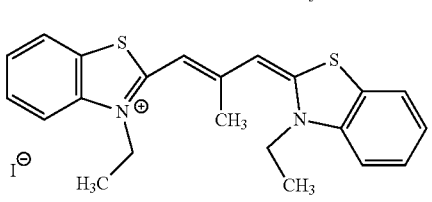

(6)
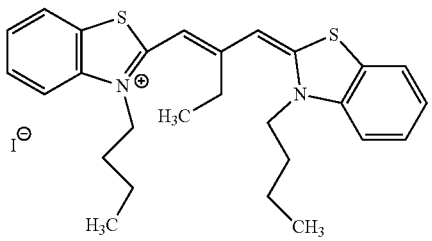

(7)
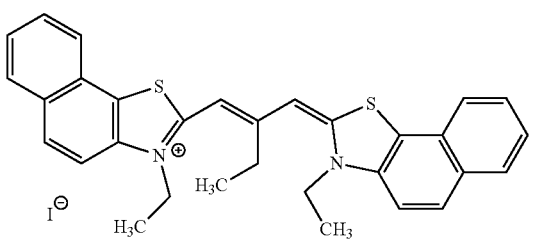

(8)
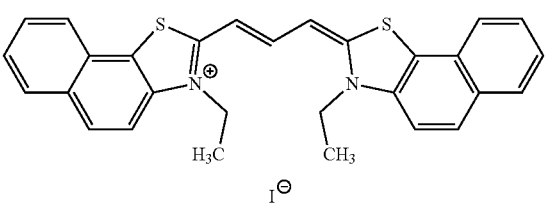

(9)
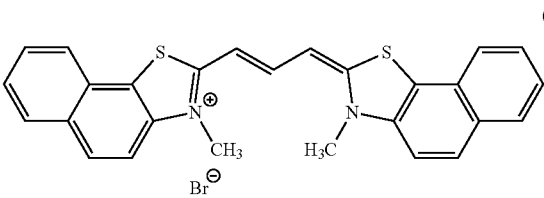

(10)
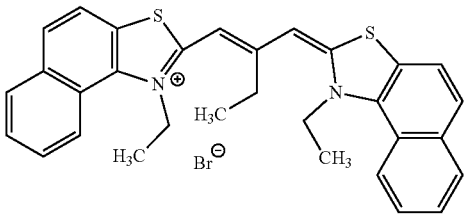

(11)
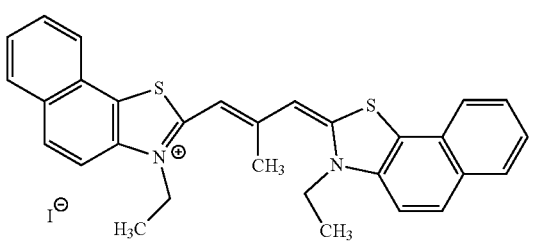

-continued

-continued
(27)
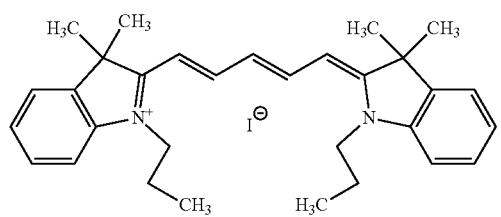
(28)
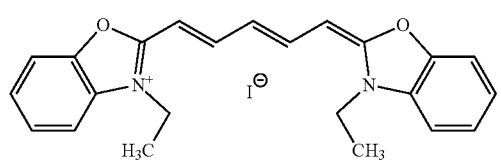
(29)
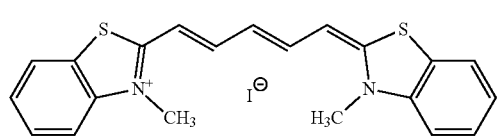
(30)
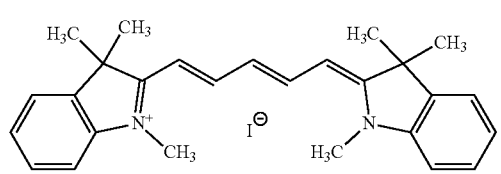
(31)
(32)
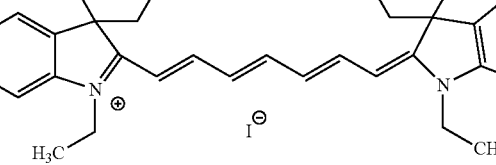
(33)
(34)
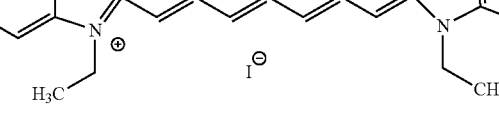
-continued
(35)
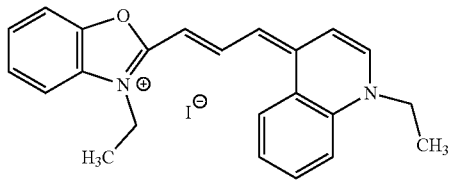
(36)
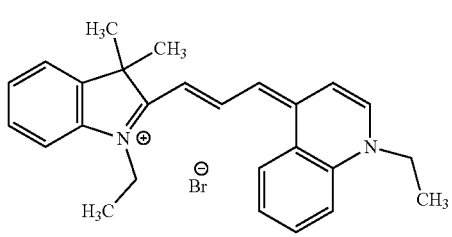
(37)
(38)
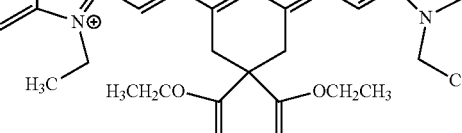
(39)
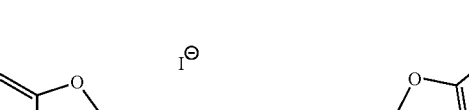
(40)
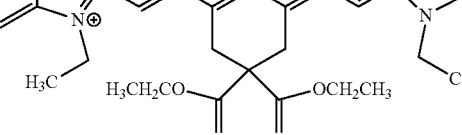
(41)
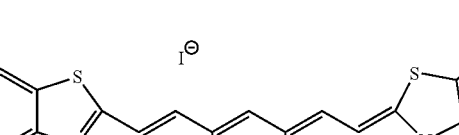

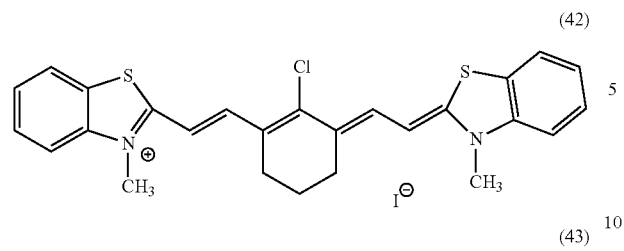
(42)
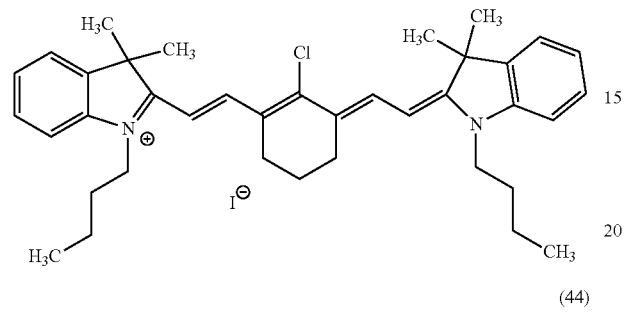
(43)
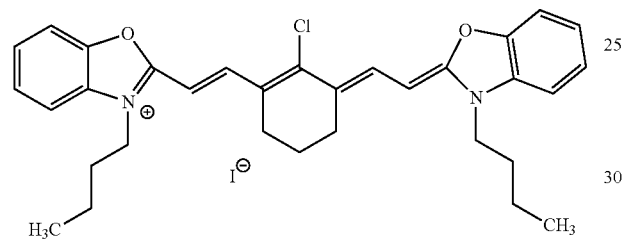
(44)
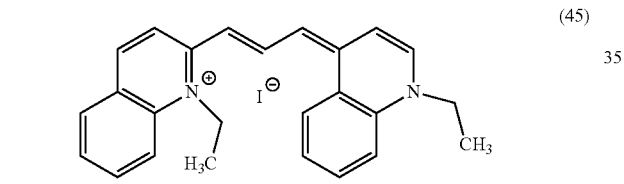
(45)
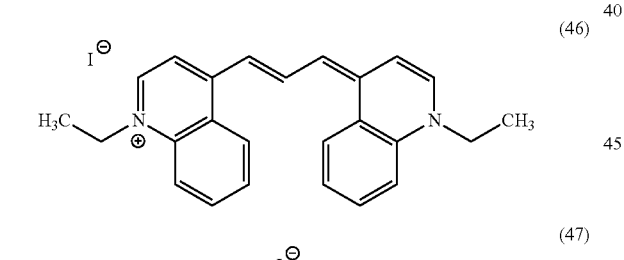
(46)
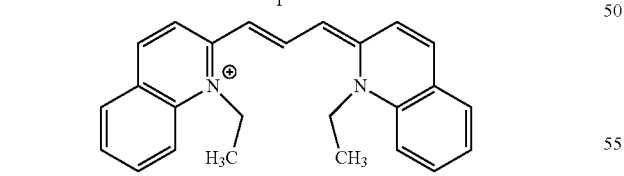
(47)
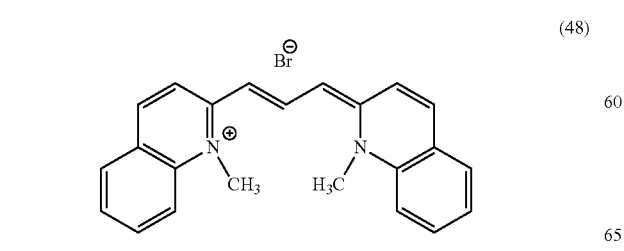
(48)
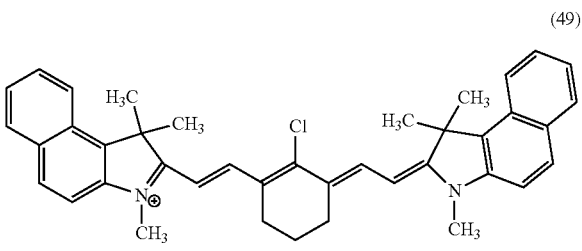
(49)
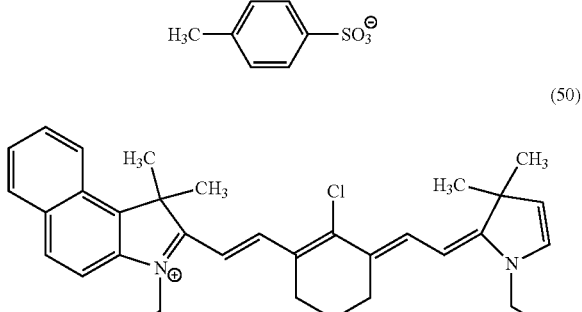
(50)
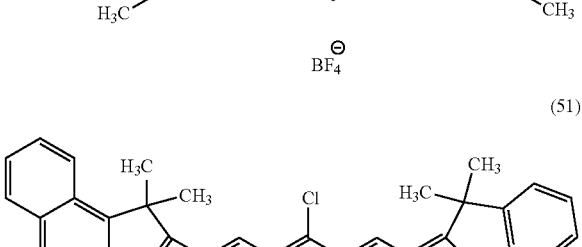
(51)
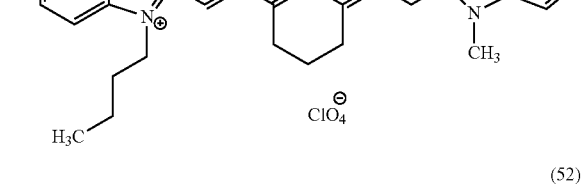
(52)
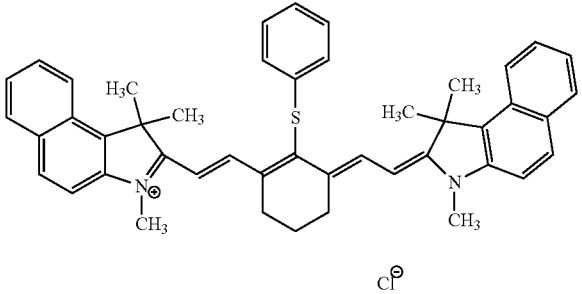
(53)

(54)
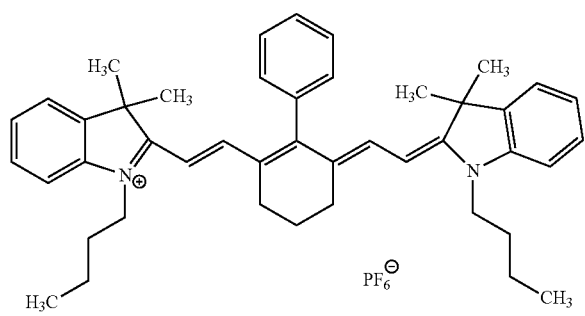

(55)
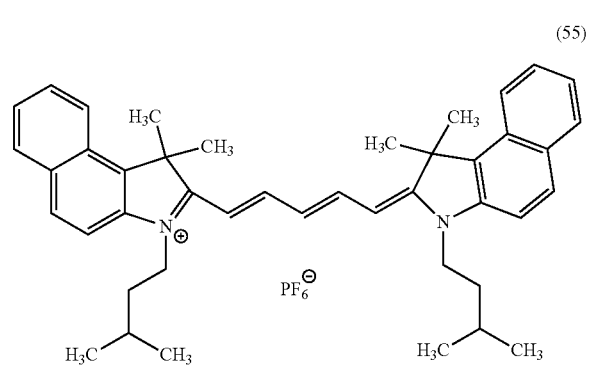

(56)
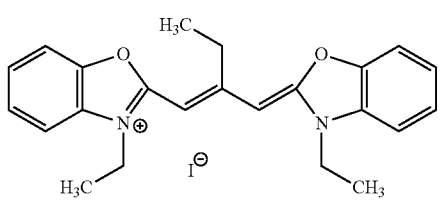

(57)
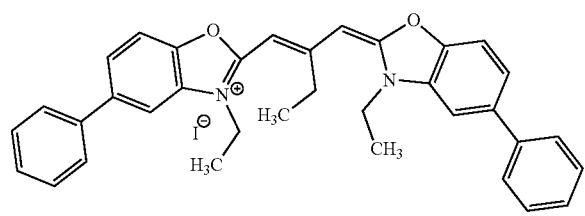

(58)
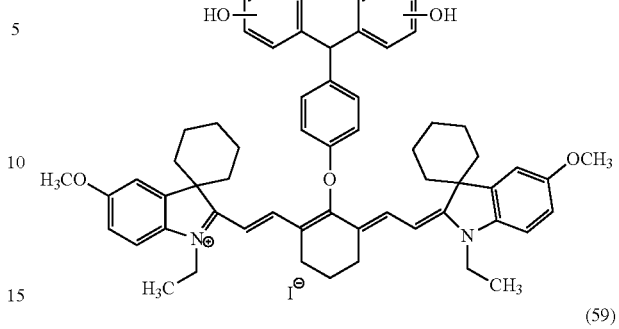

(59)

(60)
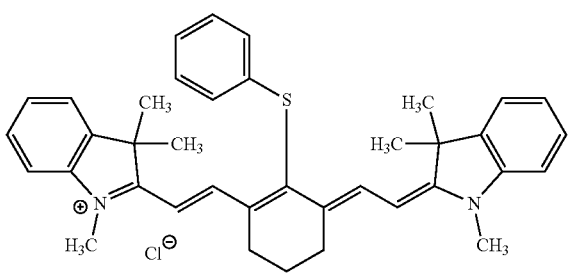

5. The method according to claim 3, further comprising detecting fluorescent intensity derived from the compound.

6. The method according to claim 3, wherein the subject is a transplanted model animal.

7. The method according to claim 3, wherein the detecting of the composition taken into the cancer stem cell is done in vivo.

8. The method according to claim 3, further comprising applying excitation light to the subject and obtaining a fluorescent image of the subject.

9. The method according to claim 3, further comprising detecting light intensity derived from the compound.

10. The method according to claim 1, wherein the subject is a vertebrate animal, an amphibian, or a mammal.

11. The method according to claim 3, wherein the subject is a vertebrate animal, an amphibian, or a mammal.

12. The method according to claim 4, wherein the subject is a vertebrate animal, an amphibian, or a mammal.

* * * * *